(12) United States Patent  (10) Patent No.: US 8,801,659 B2
Mudd et al.  (45) Date of Patent: Aug. 12, 2014

(54) INJECTION DEVICE FOR SOFT-TISSUE AUGMENTATION FILLERS, BIOACTIVE AGENTS AND OTHER BIOCOMPATIBLE MATERIALS IN LIQUID OR GEL FORM

(75) Inventors: Christopher S. Mudd, Goleta, CA (US); Ahmet Tezel, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 744 days.

(21) Appl. No.: 12/994,568

(22) PCT Filed: Jun. 1, 2009

(86) PCT No.: PCT/US2009/045831
§ 371 (c)(1),
(2), (4) Date: Jan. 24, 2011

(87) PCT Pub. No.: WO2009/158145
PCT Pub. Date: Dec. 30, 2009

(65) Prior Publication Data
US 2011/0137286 A1  Jun. 9, 2011

Related U.S. Application Data

(60) Provisional application No. 61/057,703, filed on May 30, 2008, provisional application No. 61/074,538, filed on Jun. 20, 2008.

(51) Int. Cl.
*A61M 37/00* (2006.01)
(52) U.S. Cl.
USPC ............... 604/85; 604/89; 604/154; 604/232
(58) Field of Classification Search
USPC ............... 604/154, 156, 187, 232, 85, 87–92
See application file for complete search history.

(56) References Cited

U.S. PATENT DOCUMENTS

| 2,737,946 A | 3/1956 | Hein, Jr. |
| 2,853,070 A | 9/1958 | Maurice |
| D202,754 S | 11/1965 | Naftolin |

(Continued)

FOREIGN PATENT DOCUMENTS

| EP | 1051988 | 11/2000 |
| EP | 1486218 | 12/2004 |

(Continued)

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968, XP055055114.

(Continued)

*Primary Examiner* — Emily Schmidt
(74) *Attorney, Agent, or Firm* — Linda Fox

(57) ABSTRACT

Described herein are injection devices capable of automatically injecting substances into the soft tissue of a patient. The devices can inject low to high viscosity materials at predetermined, user selected injection rates, allowing the operator more control than a traditional syringe. The devices can allow mixing of more than one substance and/or reconstitution of a solid substance for injection. The injection devices described herein can allow the operator to easily inject one or more low to high viscosity liquid or gel soft-tissue augmentation fillers, one or more drugs, one or more other biocompatible materials, or combinations thereof.

15 Claims, 12 Drawing Sheets

(56) References Cited

U.S. PATENT DOCUMENTS

| | | |
|---|---|---|
| D214,112 S | 5/1969 | Langdon |
| D224,066 S | 6/1972 | McDonald |
| 3,720,211 A | 3/1973 | Kyrias |
| 3,807,048 A | 4/1974 | Malmin |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,529,401 A | 7/1985 | Leslie et al. |
| 4,699,612 A | 10/1987 | Hamacher |
| D303,010 S | 8/1989 | Jabbusch |
| 4,869,717 A | 9/1989 | Adair |
| 5,024,656 A | 6/1991 | Gasaway et al. |
| 5,046,506 A | 9/1991 | Singer |
| 5,100,390 A | 3/1992 | Lubeck et al. |
| 5,127,436 A | 7/1992 | Campion et al. |
| 5,141,496 A | 8/1992 | Dalto et al. |
| 5,295,980 A | 3/1994 | Ersek |
| 5,305,788 A | 4/1994 | Mayeux |
| 5,322,511 A | 6/1994 | Armbruster et al. |
| 5,344,407 A | 9/1994 | Ryan |
| 5,383,851 A | 1/1995 | Mackinnon, Jr. et al. |
| 5,405,330 A | 4/1995 | Zunitch et al. |
| D378,939 S | 4/1997 | Smith et al. |
| 5,690,618 A | 11/1997 | Smith et al. |
| 5,817,033 A | 10/1998 | DeSantis et al. |
| D424,194 S | 5/2000 | Holdaway et al. |
| D441,077 S | 4/2001 | Garito et al. |
| 6,231,552 B1 | 5/2001 | Jentzen |
| 6,432,046 B1 | 8/2002 | Yarush et al. |
| 6,613,010 B2 | 9/2003 | Castellano |
| 6,616,448 B2 | 9/2003 | Friedman |
| D483,116 S | 12/2003 | Castellano |
| 6,689,095 B1 | 2/2004 | Garitano et al. |
| 6,783,514 B2 | 8/2004 | Tovey et al. |
| 6,824,526 B2 | 11/2004 | Castellano |
| 7,018,356 B2 | 3/2006 | Wise et al. |
| 7,419,472 B2 | 9/2008 | Hibner et al. |
| 7,494,473 B2 | 2/2009 | Eggers et al. |
| D615,192 S | 5/2010 | Mudd et al. |
| 7,878,981 B2 | 2/2011 | Strother et al. |
| D637,287 S | 5/2011 | Mudd et al. |
| 8,029,460 B2 | 10/2011 | Rush et al. |
| 8,066,629 B2 | 11/2011 | Dlugos |
| 8,480,630 B2 | 7/2013 | Mudd et al. |
| 8,535,278 B2 | 9/2013 | Mudd et al. |
| 8,562,571 B2 | 10/2013 | Mudd |
| 8,603,028 B2 | 12/2013 | Mudd et al. |
| 2002/0010433 A1 | 1/2002 | Johnson et al. |
| 2002/0151843 A1 | 10/2002 | Correa et al. |
| 2003/0144632 A1 | 7/2003 | Hommann et al. |
| 2003/0199883 A1 | 10/2003 | Laks |
| 2004/0010224 A1* | 1/2004 | Bodmeier ............ 604/82 |
| 2004/0092927 A1 | 5/2004 | Podhajsky et al. |
| 2004/0147883 A1 | 7/2004 | Tsai |
| 2005/0085767 A1 | 4/2005 | Menassa |
| 2005/0131353 A1 | 6/2005 | Mossanen-Shams et al. |
| 2005/0137496 A1 | 6/2005 | Walsh et al. |
| 2005/0261633 A1 | 11/2005 | Khalaj |
| 2006/0079765 A1 | 4/2006 | Neer |
| 2006/0089594 A1 | 4/2006 | Landau |
| 2007/0083155 A1 | 4/2007 | Muller |
| 2007/0100363 A1 | 5/2007 | Dollar et al. |
| 2007/0212385 A1 | 9/2007 | David |
| 2007/0250010 A1 | 10/2007 | Hohlfelder et al. |
| 2008/0033347 A1 | 2/2008 | D'Arrigo et al. |
| 2008/0097325 A1 | 4/2008 | Tanaka et al. |
| 2008/0108952 A1 | 5/2008 | Horvath et al. |
| 2008/0188816 A1 | 8/2008 | Shimazaki et al. |
| 2008/0200758 A1 | 8/2008 | Orbay et al. |
| 2009/0088703 A1 | 4/2009 | Azar |
| 2009/0124996 A1 | 5/2009 | Heneveld et al. |
| 2009/0143746 A1 | 6/2009 | Mudd et al. |
| 2009/0240200 A1 | 9/2009 | Heneveld et al. |
| 2009/0299328 A1 | 12/2009 | Mudd et al. |
| 2010/0069848 A1 | 3/2010 | Alferness et al. |
| 2010/0152675 A1 | 6/2010 | McClintock |
| 2010/0152679 A1 | 6/2010 | Tezel et al. |
| 2010/0280488 A1 | 11/2010 | Pruitt et al. |
| 2010/0282774 A1 | 11/2010 | Greter et al. |
| 2011/0021905 A1 | 1/2011 | Patrick et al. |
| 2011/0092916 A1 | 4/2011 | Tezel et al. |
| 2011/0160674 A1 | 6/2011 | Holmes et al. |
| 2013/0131632 A1 | 5/2013 | Mudd et al. |
| 2013/0131633 A1 | 5/2013 | Mudd et al. |
| 2013/0274670 A1 | 10/2013 | Mudd et al. |
| 2013/0310763 A1 | 11/2013 | Mudd |

FOREIGN PATENT DOCUMENTS

| | | |
|---|---|---|
| EP | 1923086 | 5/2008 |
| EP | 2335755 | 6/2011 |
| WO | WO 99/48601 | 9/1999 |
| WO | 2005095225 | 10/2005 |
| WO | WO 2008/019265 | 2/2008 |
| WO | WO 2008/079824 | 7/2008 |
| WO | WO 2009/098666 | 8/2009 |
| WO | WO 2009/158145 | 12/2009 |

OTHER PUBLICATIONS

Park et al., "Biological characterization of EDC-crosslinked collagen-hyaluronic acid matrix in dermal tissue restoration", Biomaterials, Elsevier Science Publishiers BV, vol. 24, No. 9, Apr. 1, 2003, pp. 1631-1641, XP004404219.

Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163, XP002574140.

* cited by examiner

INJECTION DEVICE FOR SOFT-TISSUE AUGMENTATION FILLERS, BIOACTIVE AGENTS AND OTHER BIOCOMPATIBLE MATERIALS IN LIQUID OR GEL FORM

CROSS REFERENCE TO RELATED APPLICATIONS

This is a national stage application under 35 U.S.C. §371 of PCT patent application PCT/US09/45831, filed on Jun. 1, 2009, which claims the benefit of U.S. Provisional Patent Application No. 61/057,703 filed on May 30, 2008, and U.S. Provisional Patent Application No. 61/074,538 filed on Jun. 20, 2008, the disclosure of each of which is incorporated herein in its entirety by this specific reference.

FIELD OF THE INVENTION

The present invention relates to devices useful for injecting soft-tissue augmentation fillers, bioactive agents and other biocompatible materials.

BACKGROUND OF THE INVENTION

The injection of bioactive agents and tissue augmentation fillers is quite commonplace. Commonly, bioactive agents and tissue augmentation fillers are injected manually using traditional hypodermic syringes with manual plungers. One monumental problem with traditional syringes is that they are difficult to properly utilize due to their poor ergonomics.

Another problem commonly encountered when using hypodermic syringes with manual plungers is the difficulty of controlling the rate of injection, especially when the injectable substance is highly viscous, the tissue being injected into is dense or a combination of the two. In such cases, the force required to extrude the injectable substance into a patient makes controlling the rate of injection and the handling of the syringe strikingly difficult. Commonly, unreliable injection speeds are encountered as well as patient pain associated with additional axial force on the syringe in an effort to supply sufficient extrusion force to the syringe's plunger to force the injectable substance out of the needle into the patient's tissues.

Another problem with injectable substances relates to reconstitution prior to injection. Certain substances need to be reconstituted immediately prior to injection. Patient discomfort with injections can lie in anticipation of the injection itself, and therefore, lead to a tense patient and hence more discomfort upon injection. As such, manually reconstituting an injectable just prior to injection can cause both mental and physical discomfort for a patient. A device that can automatically reconstitute injectables within the device itself just prior to injection would be a promising technology.

SUMMARY OF THE INVENTION

Accordingly, hand-held injection devices for soft tissue are provided. In an exemplary embodiment of the invention, an injection device is provided which generally comprises a cartridge suitable for containing an injectable material and couplable to a needle, a body or shell structured to contain the cartridge, a drive mechanism including a motor and a piston for moving the injectable material from the cartridge through the needle, a power source, for example a battery contained in the shell, for activation the drive mechanism; and a user programmable controller coupled to the drive mechanism, where a user-defined injection rate can be set. Advantageously, in this exemplary embodiment, the device is capable of injecting the injectable material at the user-defined injection rate from the cartridge and through the needle at a force of up to about 50 Newtons (N), for example, up to 100 N, for example, up to 200 N or more. The cartridge may be substantially cylindrical in shape and may have an inner diameter of between about 0.25 inch to about 1 inch, or between about 0.18 inch to about 0.35 inch.

Further, the device is structured to be capable of delivering, or injecting, precisely defined volumes of materials, for example, relatively high viscosity materials, such as dermal fillers, at said user-defined injection rates. For example, the device is especially advantageous for enabling controlled injection of precise volumes of cross-linked hyaluronic acid based dermal fillers into soft tissue at a substantially constant rate.

In some embodiments, the device is structured as a self-contained, hand-held device which requires no external wiring, external power source, conduits nor other external components for operation. The device conveniently requires only single hand operation and is sufficiently lightweight so as to be easily maneuverable by a physician.

Advantageously, many of the present devices are structured to provide highly controlled, precisely quantified injection of materials through very fine needles, wherein such materials are extremely difficult to inject, or even impossible to inject, using conventional techniques and manually operated syringes.

The controller may be configured to be capable of allowing a user to set a predefined, user-selected, injection rate for the material. A range of injection rates available for selection may be, for example, any injection rate defined between about 0.001 mL/sec and about 1 mL/sec. In addition, the injection device is capable of injecting the material at the user defined injection rate through a needle having a gauge of at least about 10 G and up to about 50 G, for example, a needle having a gauge between about 23 G to about 34 G, for example, between about 27 G to about 32 G. The needles may have a length of between about ¼ inch to about 2 inches, or between about ½ inch to about 1½ inches.

For example, many of the devices in accordance with the invention are designed to allow the user, for example, physician, to easily inject precise amounts of low to high viscosity liquids or gel soft-tissue augmentation fillers, one or more bioactive agents, one or more other biocompatible materials, or combinations thereof (hereinafter sometimes, collectively referred to as "injectable material") at pre-selected injection rates.

In another aspect of the invention, methods are provided for injecting materials, for example, viscous materials such as dermal fillers, into a soft tissue of a patient. In one embodiment, a method for injecting a material into soft tissue is provided which generally comprises the steps of providing a motorized injection device having a needle, providing a cartridge containing a dermal filler material to be injected into soft tissue of a patient, programming a user-defined injection rate of the material into the device, inserting the cartridge into the device, and using the device to inject the material from the cartridge and through the needle and into the soft tissue of the patient at the programmed injection rate. Advantageously, the device may be structured to be capable of injecting the injectable material at the user-defined injection rate at a force of between about 50 Newtons to about 200 Newtons or greater.

In yet another aspect of the invention, a method of injecting a material into soft tissue is provided, wherein the method comprises the steps of providing a motorized injection device containing a first material and a second material separated from the first material, and, within the device, mixing the first material with the second material to create a product to be injected into soft tissue of a patient. The method further comprises programming a user-defined injection rate of the product into the device and using the device to inject the product into the soft tissue of the patient at the programmed injection rate. In a specific embodiment, the first material is a dry material, for example, a powder or lyophilized material and the second material is a liquid, for example, saline, a solvent or a liquid suitable for reconstituting the first material.

In one aspect of the invention, the injectable material is selected from the group consisting of dermal fillers, hyaluronic acid-based dermal fillers, hydrogels, organogels, xerogels, encapsulated and/or cross-linked biomaterials, silicones, glycosaminoglycans, polysaccharides, collagen, elastin, local anesthetics, drugs, bioactive agents, antioxidants, enzyme inhibitors, vitamins, minerals, water, saline, light curable or light activated materials, pH curable or pH activated materials and botulinum toxin.

In one embodiment, the soft tissue is selected from the group consisting of skin, muscles, glands, ducts, tendons, follicles, and combinations thereof. In another embodiment, the skin is located on an area selected from the group consisting of face, neck, arms, underarms, legs, buttocks, abdomen, back, breasts, scalp, feet, and hands.

In one embodiment, a method is described for injecting a solid bioactive agent into a soft tissue comprising: providing an injection device comprising an inner body, and outer body and a needle; providing a solid to be injected into the patient wherein the solid is housed within the inner body of the device; mixing the solid with a solvent thereby reconstituting the solid and forming a product to be injected; and using the device to inject the product through the needle into the patient with an extrusion force great enough to deliver the product to the soft tissue at a rate programmed into the device before injection.

In one embodiment, the injectable material is selected from the group consisting of dermal fillers, hyaluronic acid-based dermal fillers, hydrogels, organogels, xerogels, encapsulated and/or cross-linked biomaterials, silicones, glycosaminoglycans, polysaccharides, collagen, elastin, local anesthetics, drugs, bioactive agents, antioxidants, enzyme inhibitors, vitamins, minerals, water, saline, light curable or light activated materials, pH curable or pH activated materials and botulinum toxin.

DEFINITION OF TERMS

Digits: As used herein "digits" shall refer to the fingers of a human. Each digit or finger can be referred to separately or in combination. Digit 1 is commonly referred to as the thumb. Digit 2 is commonly referred to as the index finger. Digit 3 is commonly referred to as the middle finger. Digit 4 is commonly referred to as the ring finger. Digit 5 is commonly referred to as the pinky finger.

BRIEF DESCRIPTION OF THE DRAWINGS

Many of the advantages and features of the present invention may be better appreciated and more clearly understood with reference to the following detailed description and the accompanying drawings of which.

DETAILED DESCRIPTION OF THE INVENTION

Described herein are novel injection devices that allow a user, for example, a physician, to inject one or more low to high viscosity liquid or gel soft-tissue augmentation fillers, one or more bioactive agents, one or more other biocompatible materials, or combinations thereof in a precisely controlled manner. In some embodiments, the present devices allow the injection of materials that are difficult or impossible to inject with a traditional manual hand held syringe.

The devices described herein allow the operator to easily inject a material through any size needle known in the art by depressing a button. The devices are easy to hold, manipulate and operate with one hand, and in some cases adjust easily with the operator's opposing hand. The devices allow the operator to set a precise injection speed or extrusion rate of the material to be injected. The devices can also indicate the initial volume, volume injected and remaining volume of the material being delivered to a patient.

In one embodiment, the devices are comprised of an outer shell and an inner body. The inner body houses one or more user-replaceable cartridges, one or more internal drive mechanisms and any other internal mechanisms described infra.

The devices can conceivably be used to inject an injectable material into any suitable location of a patient's body. In one embodiment, the devices described herein are used to inject materials into the patient's soft tissue. In a further embodiment, the soft tissue is the patient's skin. In other embodiments, the soft tissue can be muscles, glands, ducts, tendons, follicles, and the like. The device can be used to inject materials into, for example, the face, neck, arms, underarms, legs, buttocks, abdomen, back, breasts, scalp, feet and/or hands.

The Outer Shell

The devices described herein comprise an outer shell. The outer shell has an ergonomic shape that facilitates manipulation of the device. Additionally, the present devices can accommodate operator hands of different sizes. Hand size accommodation can be accomplished by different device sizes, position-adjustable device handgrips or interchangeable device handgrips. For example, interchangeable device handgrips can come in various predetermined sizes or can be personalized for a particular user. In one embodiment, the device handgrip can slide along a rail forward or backward relative to the outer shell and be locked into place. In another embodiment, the device handgrip can be unlocked, removed and re-attached in another position on the outer shell.

Four exemplary, outer shell shapes suitable for use as part of the present devices are depicted in FIGS. 1-3 and 8.

Figure 1A:
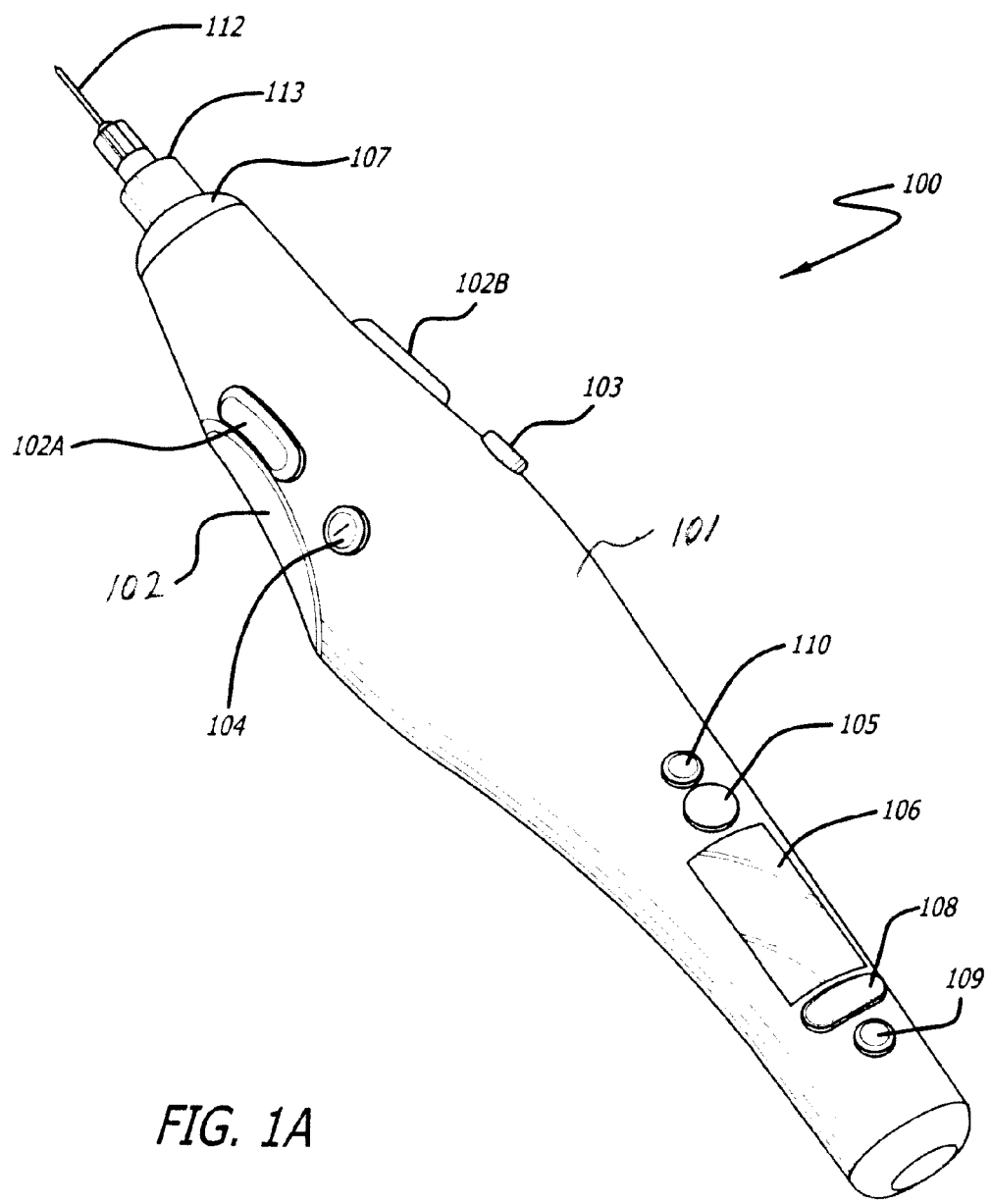
FIGS. 1A, 1B and 1C are perspective, top and side views, respectively, of an embodiment of a programmable injection device in accordance with the invention.
Figures 1B, 1C:
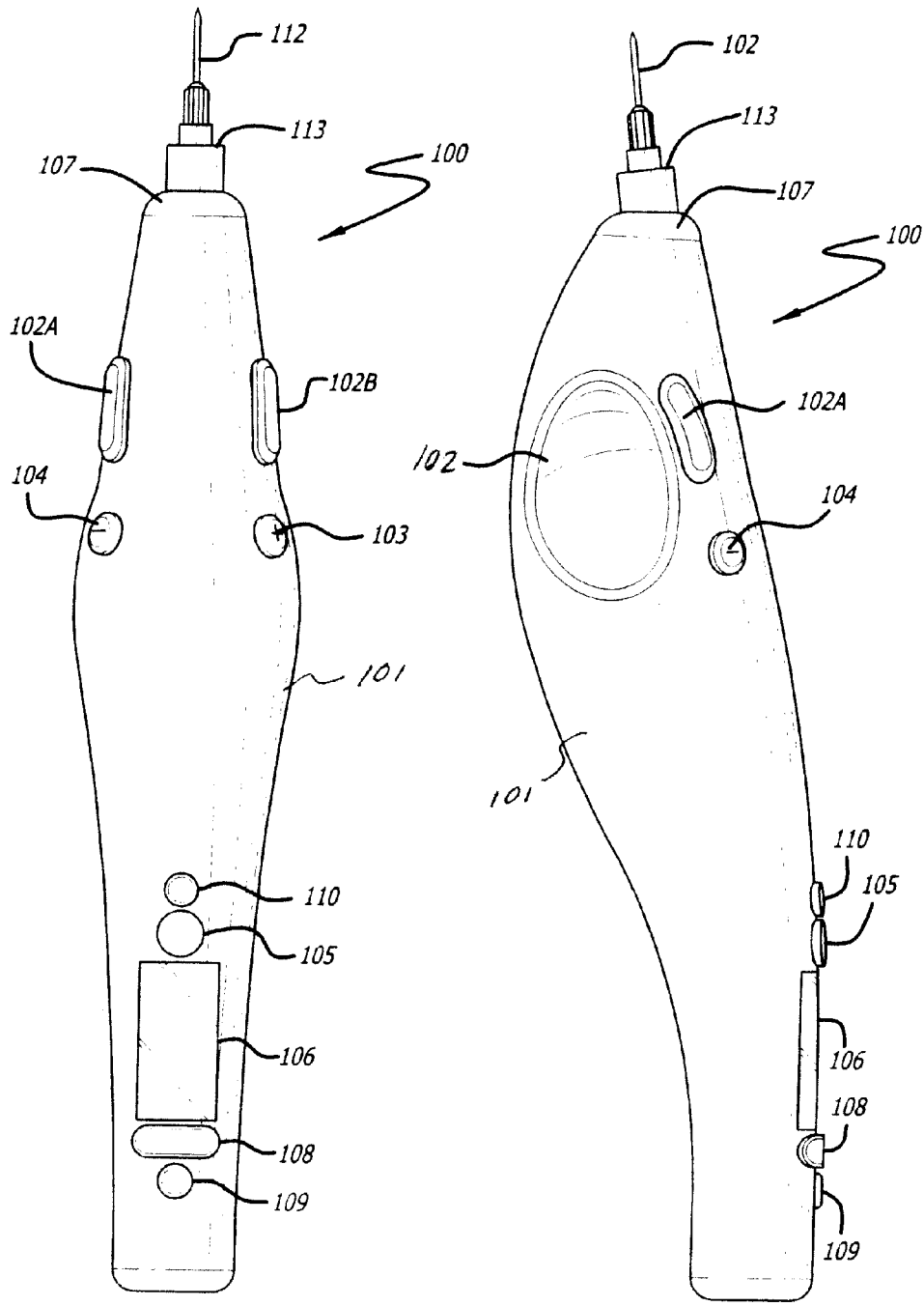

FIGS. 1A, 1B and 1C depict three different views of a device 100 in accordance with an embodiment of the invention. Device 100 is a somewhat pen style design. Device 100 includes a shell 101 structured to be held by the operator in a similar manner to that of a writing instrument. Device 100 is held such that the operator's thumb may be positioned in a finger grip 102, the index finger is positioned such that it may engage inject button 102A and/or 102B and injector speed adjustment buttons 103 and or 104. The weight of device 100 rests on the middle finger and the hand between the thumb and index finger. The device 100 can be used by both right and left handed operators as there are mirrored finger grips 102 and injection buttons 102A and 102B on both sides of the device 100. It can be appreciated that with suitable modification to device 100 within the scope of the invention, device 100 can be designed to be specifically used by a right handed operator. Similarly, the device 100 can be modified within the scope of the invention to be specifically used by a left handed operator.

The device 100 is powered on and off using power button 105. The device further comprises a display 106 to provide information about the device for reference by the operator. The information on display 106 can be adjusted using menu driven multi-button 108 and confirmed using button 109.

A cartridge (not shown in FIGS. 1A, 1B and 1C) containing material to be injected can be installed into the device 100 by removing end cap 107, inserting cartridge into shell 101 and reinstalling end cap 107. The cartridge is couplable to a needle 112 by means of a luer tip 113.

Figure 2A:
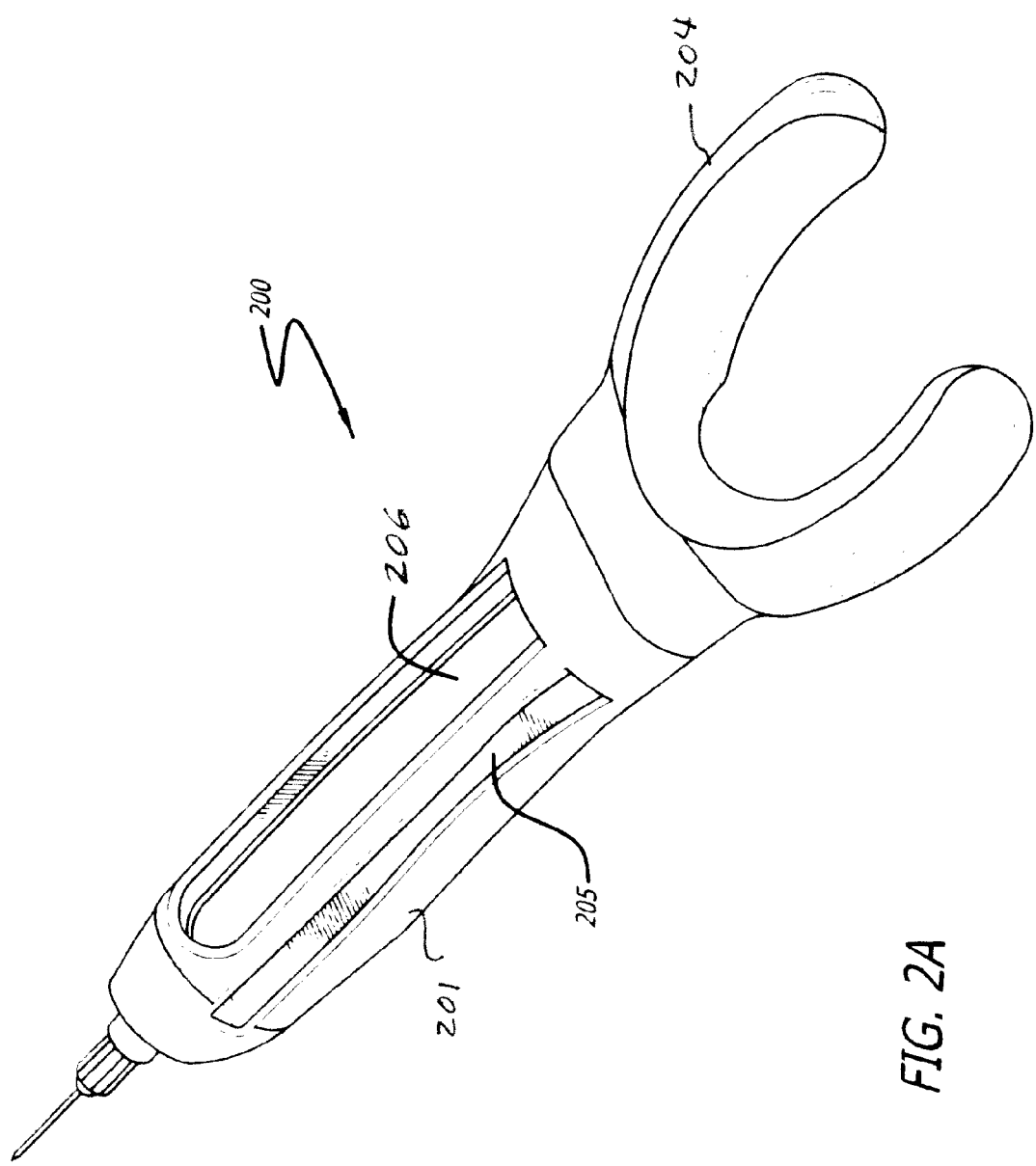
FIGS. 2A and 2B are perspective views of another embodiment of the invention.
Figure 2B:
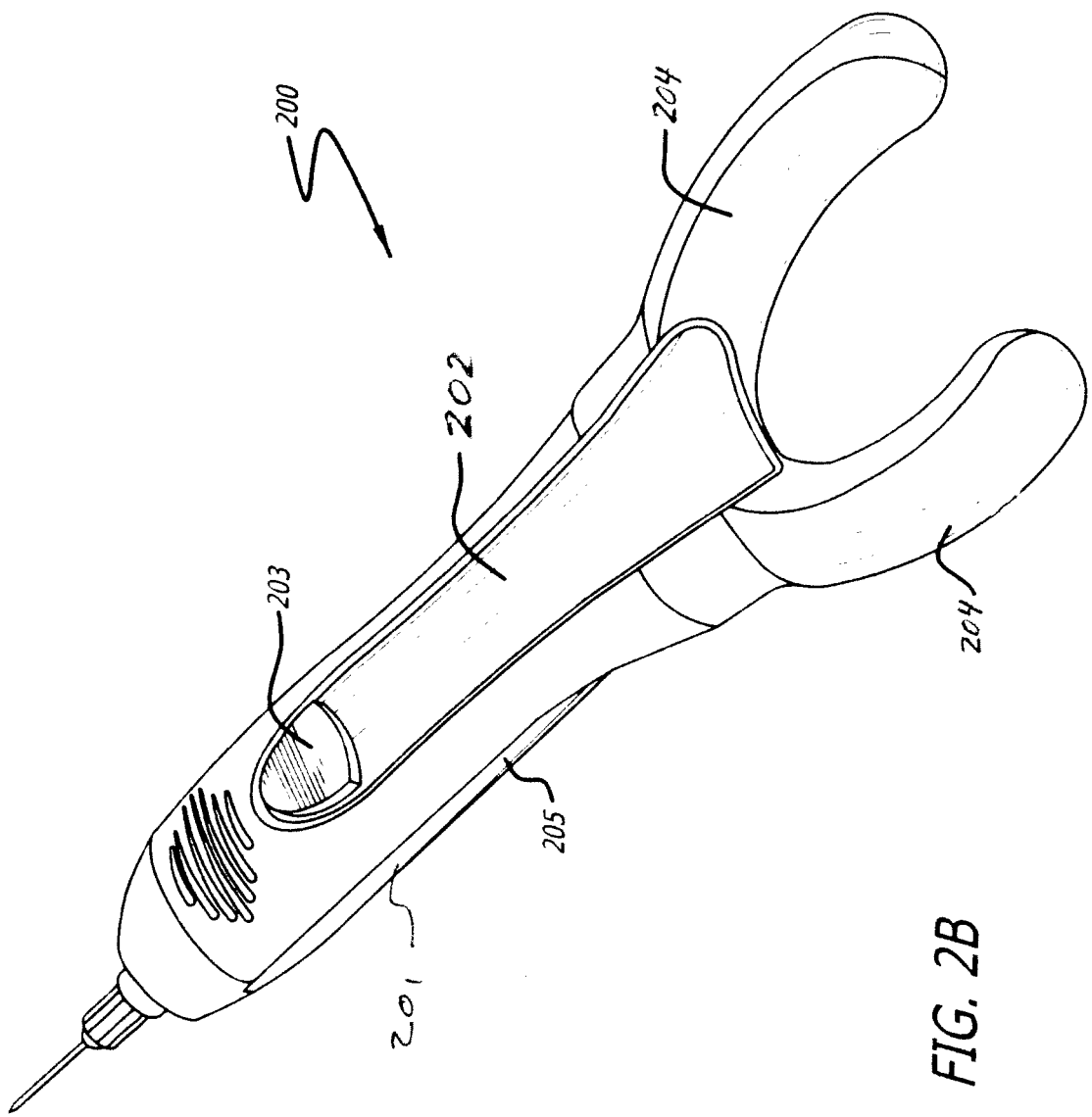

FIGS. 2A and 2B depict another device 200 in accordance with the invention which may be substantially the same as device 100 with the exception of the shape of the shell 201. Shell 201 is shaped to generally conform to a finger of the user/operator. In one embodiment, the finger is an index finger (digit 2). The top of the device 200 has a depression 202 for the index finger to fit comfortably on device, with an injection button 203 situated to be located at the end of the finger. The thumb (digit 1) and the middle finger (digit 3) can be placed comfortably against the two opposing sides of such a device to aid in control. However, it is conceivable that such a device can be operated using any finger (digit 1-5) the operator feels comfortable with and any combination of other fingers used for supporting the device. The proximal end of the device comprises a "U" shaped appendage 204 wherein the finger is inserted and which rests on the hand at the base of the finger. The appendage 204 can be constructed of a flexible material which can be formed to the particular operator's finger length and circumference. Finger length accommodation can be accomplished by physically different device sizes or adjustable device lengths and/or widths. The device can also comprise a side window 205 and/or a bottom window 206, running the length of the bottom side of the device 200.

Figure 3:
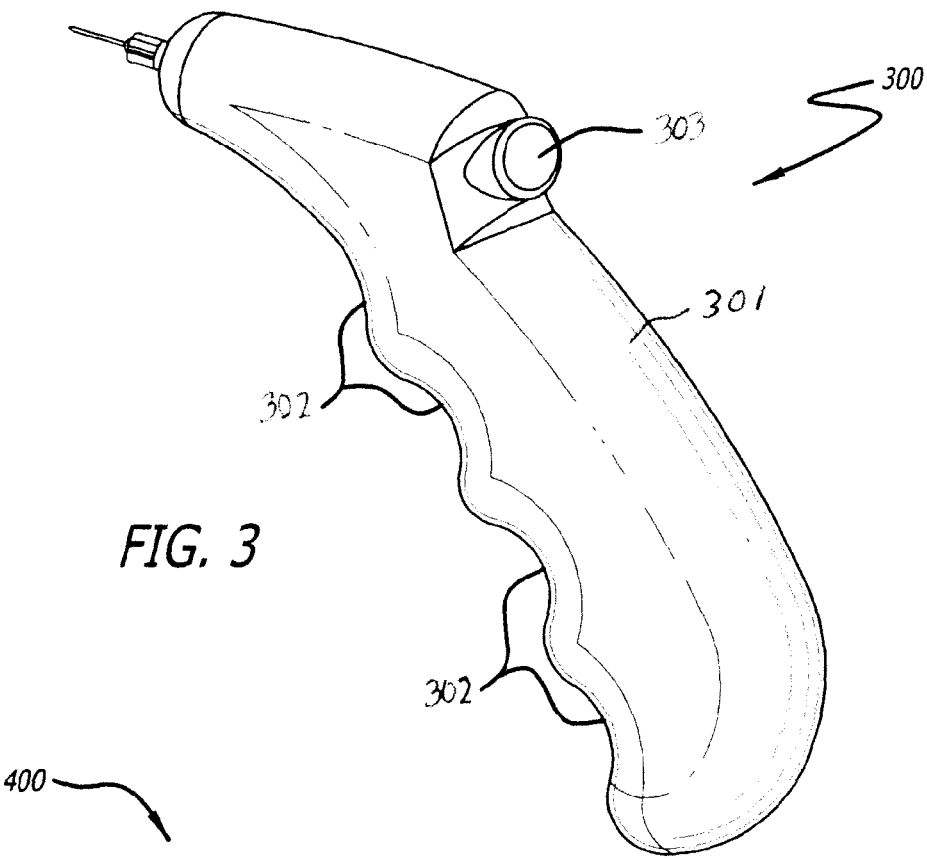
FIG. 3 is a perspective view of yet another embodiment of the invention.

FIG. 3 depicts another embodiment of the invention, for example, wherein a shell 301 of the device 300 has a pistol-grip style design. Device 300, which is held firmly in an operator's hand using finger grips 302. Digits 2-5 can fit snugly into finger grips 302. Digit 1 can remain free to engage inject button 303. The shell 301 may comprise a window or additional opening wherein the operator can view the volume of the injectable material in the cartridges.

FIGS. 8A and 8B depict another device 800 in accordance with the invention. Device 800 comprises shell 800a including handle 801. Inject buttons 802 and/or 803 can be engaged by the index finger of the operator, the button used depending on which is most comfortable to use for the operator, for example, depending upon whether the operator is right or left handed. Eject button 804 is easily operated by either a right or left handed user (a similar button is located on the opposite side of the device) to eject the cartridge (not shown). A power/menu button 805 can be provided to control the power to the device by holding button 805 down or can operate menus displayed on display 806 and adjusted by selector button 807. Needle 808 is connected to cartridge 809 via a luer style connection which, in one embodiment, can inserted into the device 800 through the front of the device and snapped into place within the device 800, similar to that of the device 100 shown in FIG. 1A-1C.

The shells 101, 201, 301, 800a of devices 100, 200, 300 and 800 respectively, can be comprised of any suitable materials such as, but not limited to, rigid thermoplastics, thermoplastic elastomers, silicones, glass, metals, composite materials, carbon fillers, or any combination thereof.

Depending on the particular application, it may be desirable for the devices 100, 200, 300, 800 to be routinely sterilized by means commonly known in the art. Therefore, the components of the devices may be made of materials that are known to withstand sterilization techniques such as, but not limited to, dry heat, steam (autoclave), ethylene oxide treatment, gamma radiation, ultra violet (UV) light or combinations thereof including other methods known in the art. The devices can also be constructed of materials that can be cleaned with soap and water or antiseptic materials.

The shells 101, 201, 301, 800a may include one or more various ergonomic features such as detents, depressions and/or extrusions. The features further allow the devise to be easily held, manipulated and operated with one hand, or if necessary, adjustments can be made with the opposing hand. In one aspect of the invention, each of devices 100, 200, 300 and 800 can be structured to be substantially entirely self-contained, requiring no external power source, conduits or other external components for operation.

In addition to, or in lieu of the button functions already herein described, button functions may include, but are not limited to, power (to turn the device on and off), inject (to inject the injectable material), eject (to eject a cartridge), adjustment (for injection speed or rate), menu (for electronic display screen), adjustment (electronic display screen menu options), set/accept/enter (to accept an adjustment in a menu) and combinations of button described herein.

In some embodiments, an inject button coupled to a pressure sensitive switch is provided in order that the delivery rate of the material may be adjusted based on the amount of pressure a user applies to the inject button.

In addition, it is contemplated that the outer shell of the devices may have one or more light emitting devices to indicate states of the injection device. In one embodiment, the light emitting device is a light emitting diode (LED). The LEDs can be used to indicate status of the device and can be of different colors to indicate different stages of readiness. Some non-limiting examples include an LED which is red to indicate that the device is not ready or green to indicate the device is ready. Additionally, a yellow LED can be used to indicate that the cartridge is low and needs replacing.

Each device described herein may have at least a portion sealed to prevent fluids or debris from entering the inner body of the device. Methods of sealing a medical device of this type are known in the art and can include, but are not limited to, o-rings, gaskets, sealants, silicones, thermoplastic elastomers, polymers, polymer coatings, sheaths, partial sheaths and waxes. The external buttons described supra may be sealed to prevent fluids or debris from entering the inner body of the device through the buttons location.

The devices may further comprise an electronic display screen, such as display 106 shown in device 100 in FIG. 1A-1C and display 806 shown in device 800 in FIG. 8A. Screens can include those commonly known in the art that are easily viewable by the operator including, but not limited to, organic light-emitting diode (OLED), light emitting diode (LED) or liquid crystal display (LCD). The display screen can display information about the device, about the cartridge, about the injectable material and/or about the injection itself. The screen can display some or all of the following, non-limiting, example information: company name and/or logo, device name, injectable material name and/or logo, device part number, injectable material (i.e. Product) part number, Product reference number, device lot number, Product lot number, Product volume, Product expiration date, cartridge volume, initial Product volume, remaining Product volume, Product volume injected into a specific anatomy of the patient, Product injection speed, depth of injection, needle force, needle gauge, needle length, patient name, patient identification, location of injection (patient's anatomy), date, time, language, number of uses or injections (until battery needs recharging or replacement), device status (e.g. ready, cartridge not loaded, cartridge empty, error), firmware version, power status (on, off, standby), battery power, battery power remaining, and/or battery charging status.

The information displayed on the screen may be displayed on the primary menu screen or on one or more user-selectable or user-configurable menu screens. The operator may easily customize the screen. The electronic display screen and operating system may be software or firmware upgradeable by any means known in the art.

Figure 4:
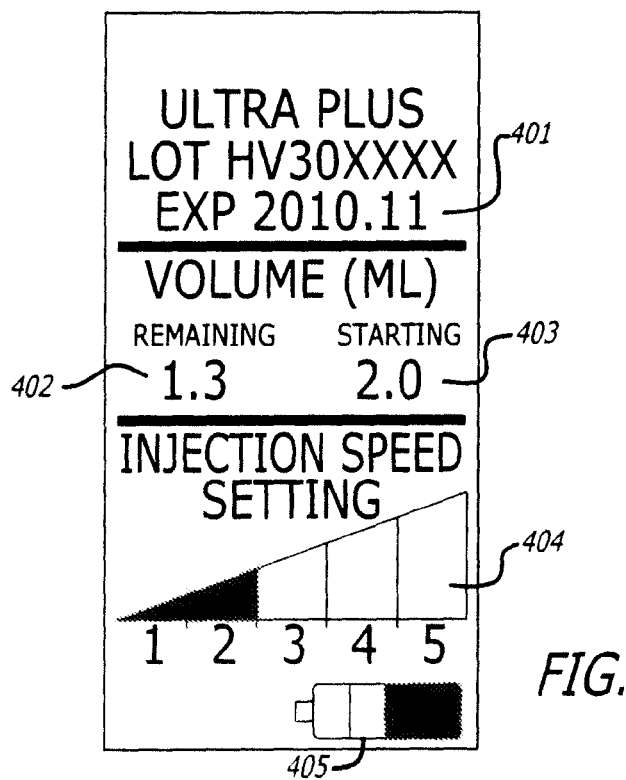
FIG. 4 shows a display screen of an injection device of any of the embodiments shown in FIGS. 1A through 4.

FIG. 4 depicts an exemplary display screen. Display screen 400 can display information such as, but not limited to, injectable material (e.g. Product) expiration date 401, volume of Product remaining 402, starting volume 403, injection speed 404, and battery power indicator 405. There are several other possible screen configurations and information that can be displayed on the screen. One skilled in the art may envision other possible configurations and pieces of information that may be useful on the screen and those configurations and pieces of information are considered within the scope of the present description.

The Inner Body

The inner body of the devices 100, 200, 300, 800 may comprise one or more of the following components used to inject the injectable material into soft tissue in a patient from the cartridge through the needle: vacuum pump, air pump, motor (e.g. gear or step motor), gears (e.g. rack and pinion system or worm gear), linear actuator, linear spine shaft, linear guide, air piston(s), springs (e.g. compression), magnets and/or replaceable compressed air cartridge.

The inner body can comprise one or more motors or actuators to move internal components. The motor(s) and/or actuator(s) can drive one or more gears and can be driven by an appropriate voltage. The motor can have a maximum stall torque of 7,500 g cm, 5,000 g cm, or 4,480 g cm. The stall torque can have a minimum of 100 g cm, 250 g cm, or 396 g cm. The maximum efficiency torque can have a maximum of 1,500 g cm, 1,000 g cm, or 900 g cm. The maximum efficiency torque can have a minimum of 50 g, 75 g cm, or 88 g cm. Further, the gear ratio of the motor and/or actuator can have a maximum of about 500:1, 350:1, or 300:1. The gear ratio of the motor and/or actuator can have a minimum of about 10:1, 25:1, 30:1, or 100:1. In one embodiment, the gear ratio can be about 298:1. In one embodiment, the motor is a Firgelli GM12-N20VA-08260-298-R gear motor (Firgelli Technologies, Inc. Victoria, BC, Canada).

Figure 5:
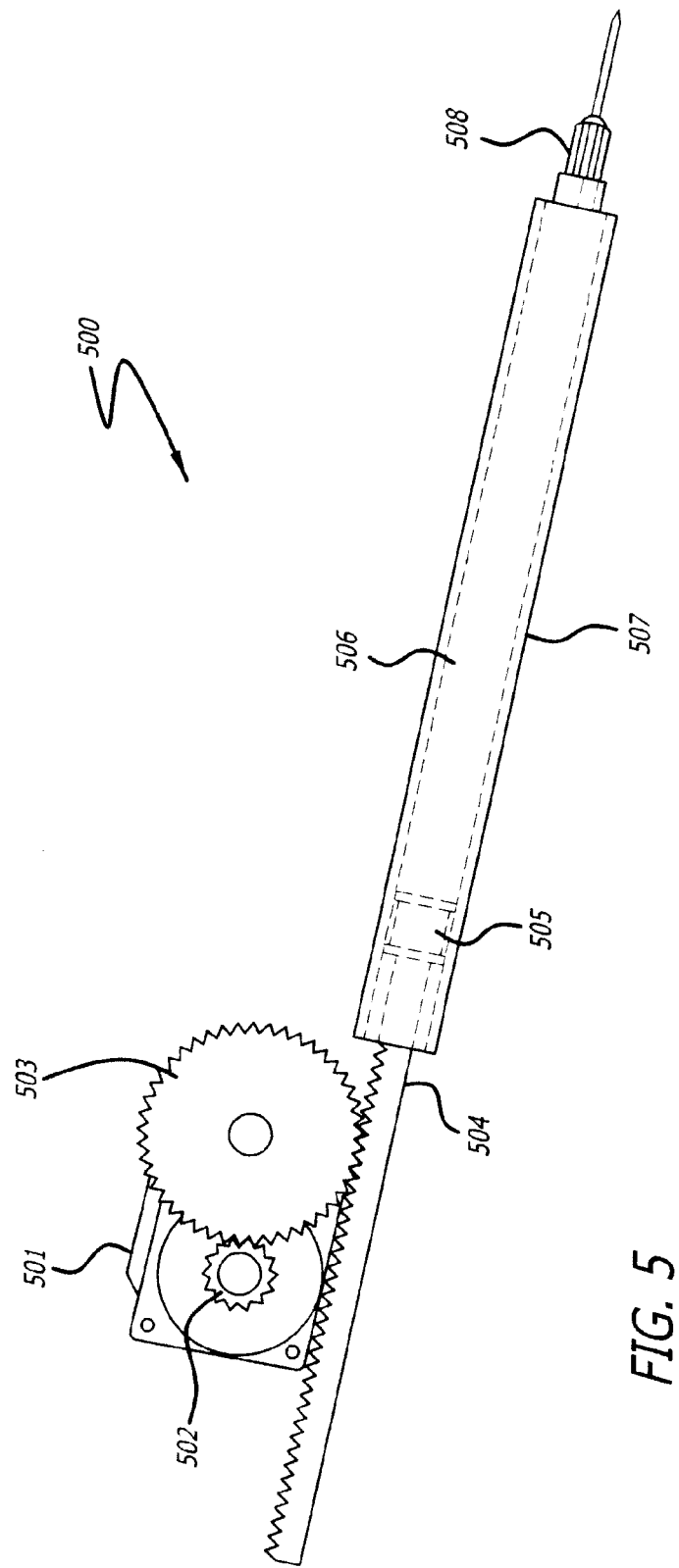
FIG. 5 shows a simplified side view of internal components of the device shown in FIGS. 1A-1C, an outer shell of the device removed for clarity.

FIG. 5 is an exemplary, non-limiting, configuration 500 of various components which may form part of device 100 shown in FIG. 1A-1C, with housing 101 removed for the sake of clarity. Device 100 may comprise, for example, cartridge 507 couplable to needle 508, and motor 501 whose driveshaft is fitted with a first gear 502. First gear 502 drives second gear 503. One skilled in the art will appreciate that there are several gear/motor combinations which can be used to achieve various linear drive speeds. In one embodiment, the device may comprise one or more worm gears. Second gear 503 drives rack 504 which engages plunger 505. Plunger 505 is driven by rack 504 through cartridge 507. As plunger 505 is driven through cartridge 507, the injectable material 506 is forced out of needle 508.

In some embodiments of the invention, device 100, 200, 300 and 800 can include features enabling the device to mix different materials, products and medicaments, or medicaments within the device and prior to injection. In one embodiment, the injectable material includes a solid or dry component, for example, a lyophilized component, and a liquid component, for example, a solvent such as saline for reconstituting the dry component prior to injection. In such a case, additional components of the device may be included. These include, but are not limited to, a vacuum pump, an air pump, a gear and/or step motor, one or more gears, a linear actuator, a linear spine shaft, a linear guide, an air piston, one or more springs, one or more magnets, and replaceable air cartridges.

Figure 6:
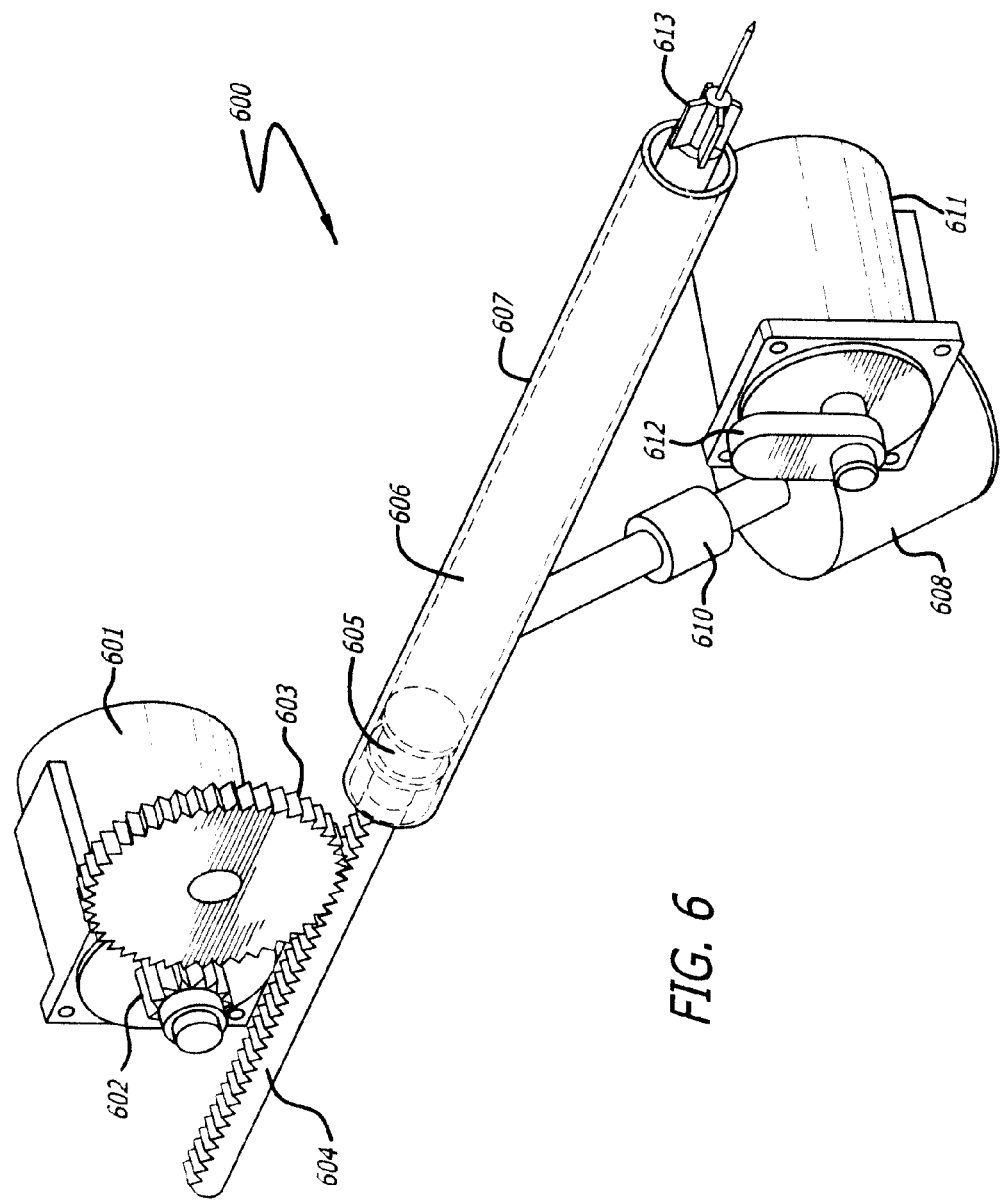
FIG. 6 is a simplified perspective view of internal components of an embodiment of the invention which allows for mixing different materials prior to injection into soft tissue.

For example, FIG. 6 is a simplified perspective view of internal components 600 of an embodiment of the invention which allows for mixing different materials prior to injection into soft tissue. It should be appreciated that any of devices 100, 200, 300 or 800 can be constructed within the scope of the invention to include internal components 600 which allows for mixing of materials prior to injection. Components 600 may include, for example, a miniaturized motor 601 including driveshaft fitted with a first gear 602 which drives second gear 603. One skilled in the art will appreciate that there are several gear motor combinations which can be used to achieve various linear drive speeds. In one embodiment, the device may comprise one or more worm gears. Second gear 603 drives rack 604 which engages plunger 605. Plunger 605 is driven by rack 604 through cartridge 607. A vial 608 of a second material can be attached to a pump (not shown), wherein the pump directs the second material through a one way valve 610 and into cartridge 607. The first material and the second material are mixed in cartridge 607. Cartridge 607 can be agitated by a vibration from a second motor 611 fitted with a weight 612. As the weight, which is out of balance, spins, the device vibrates agitating the mixture in cartridge 607. Plunger 605 is driven through cartridge 607, and the Product 606 is forced out of needle 613.

The second material can be substance used to dilute, dissolve or saturate the first material. In one embodiment, the second medicament is saline. In another embodiment, it is water. In one embodiment, it is any appropriate solvent to dissolve a solid, free-dried, freeze-dried, lyophilized, frozen, or aspirated product, or combinations thereof.

The inner body of the devices may contain microelectronics, for example, at least one printed circuit board (PCB) to control electronic functions of the device. The PCB can control the display screen, pump, motor, linear actuator and/or other powered components. The PCB can be used to regulate the current and/or voltage delivered to the various electronic parts of the devices.

In one non-limiting embodiment, the internal components may comprise a motor as described above attached to a worm gear which drives a rack. The motor, an LCD display, microswitch, insertion/ejection mechanism, and optical encoder may all be controlled by a PCB. The PCB may be powered by a battery located adjacent to the PCB.

In one embodiment, the at least one cartridge housed in the inner body of the device maybe be ejected manually, automatically, or semi-automatically. Automatic methods can be devised using one or more of the following, non-limiting components: motor (e.g. gear or stepper), gears (e.g. rack and pinion, worm or worm gear), linear actuator, air piston, springs (e.g. compression or extension) and/or magnets.

The devices described herein may contain a force or strain gauge used to measure the puncture force and depth of the needle through the patient's skin. The depth of the injection can be important for certain types of Products and their respective absorption rates. The puncture force can be instrumental to reducing injection pain as it can serve to adjust the force of the needle puncture depending on the skin type and needle gauge.

In one embodiment, the devices described herein comprise a linear variable differential transformer (LVDT). An LVDT can be used to measure liner displacement. The LVDT can be used to measure the depth of the needle through the patient's skin or tissue or can be used to measure the depth of the plunger into the cartridge, thereby measuring the amount of Product dispensed from the device.

The devices described herein may comprise a temperature controlled unit. The unit can comprise a jacket that surrounds the cartridge thereby allowing the operator to keep the Product either heated or cooled before, during, and between injections. This may be more critical for some Products more than others, for example, Products that must be kept refrigerated would benefit from this technology.

The Cartridge

The devices 100, 200, 300, 800 can comprise one or more cartridges, for example, cartridge 507 and 607 shown in FIGS. 5 and 6 respectively, for containing an injectable material. The cartridge can comprise any suitable material of construction, for example, a rigid thermoplastic, thermoplastic elastomer, silicone, glass, metal, composite materials or any combination thereof. The cartridge can have an outer diameter of about 1/16 inch to about 1 inch. The cartridge may have an inner diameter of about 1/16 inch to about 7/8 inch. The length of the cartridge can be from about 1/2 inch to about 6 inches.

The cartridge can accommodate material volumes from about 0.1 mL to about 60 mL, more preferably, about 0.1 mL to about 10 mL. The cartridge can contain a specific or predetermined amount of material to be delivered to a patient. The cartridge can have a luer-tip or slip-tip end (both commonly seen on ordinary medical syringes). An example of a luer-tip end can be seen in FIG. 5.

The cartridge can have various outer cross section designs and the inner body chamber may be designed to accommodate the designs. The outer cross section design can be selected from the following non-limiting examples: round, elliptical, rectangular, square, or polygon in shape. In a preferred embodiment, the cross section design is round. In some embodiments, the cartridge is substantially cylindrical in shape and has an inner diameter of between about 0.25 inch to about 1 inch, or between about 0.18 inch to about 0.35 inch.

In one embodiment, the cartridge has a unique shape to be used only with one of the devices described herein.

The cartridge can have a protruding or snap feature used to lock the cartridge into the inner body of the devices when it is fully inserted. This feature can also be a protruding or snap feature found on the inner body of the devices.

The cartridge can comprise a needle or is structured to be couplable to a needle. The needle may be integrated or may be an interchangeable needle. In some embodiments, the device is structured to inject material at a user defined injection rate through a needle of at least about 10 G, for example, between about 23 G and about 34 G, for example, between about 27 G and about 32 G. The length of the needles used can be any appropriate length known in the art, for example, the needle may have a length of between about 1/16 inch and about 3 inches, for example, between about 1/4 inch to about 2 inches, for example, between about 1/2 inch to about 1 1/2 inches.

The cartridge may further comprise a one-way valve. The one-way valve may comprise an adjustable orifice used to regulate the speed or force of material being injected. This one way valve may be adjustable manually or electronically, controlled by the printed circuit board (PCB) found in the inner body.

The cartridge can comprise an electronic identification tag affixed to the outside of the cartridge. In one embodiment, the electronic identification tag is a radio-frequency identification (RFID) tag. The information contained in the RFID tag can be processed by a radio-frequency reader housed in the inner body of the devices. As such, the RFID tag can contain and relay specific information to the devices when the cartridge is inserted. Exemplary information that can be stored on an RFID tag include, but is not limited to, Product name, Product reference number, Product part number, Product prescription ($R_x$) number, Product lot number, Product volume, Product expiration date, Product efficacy, Product concentration and/or Product weight. The information processed by the device can be displayed on the electronic display screen and/or stored in the device itself.

The cartridge can comprise one or more external features, such as ridges, detents and/or depressions. The external features allow the cartridge to be read and identified by optical encoder(s) and/or microswitch(es) that are housed in the inner body of the devices. Exemplary information that can be identified using external features include, but is not limited to, Product name, Product reference number, Product part number, Product Rx number, Product lot number, Product volume, Product expiration date, Product efficacy, Product concentration and/or Product weight. The information processed by the device can be displayed on the electronic display screen and/or stored in the device itself.

Figure 7:
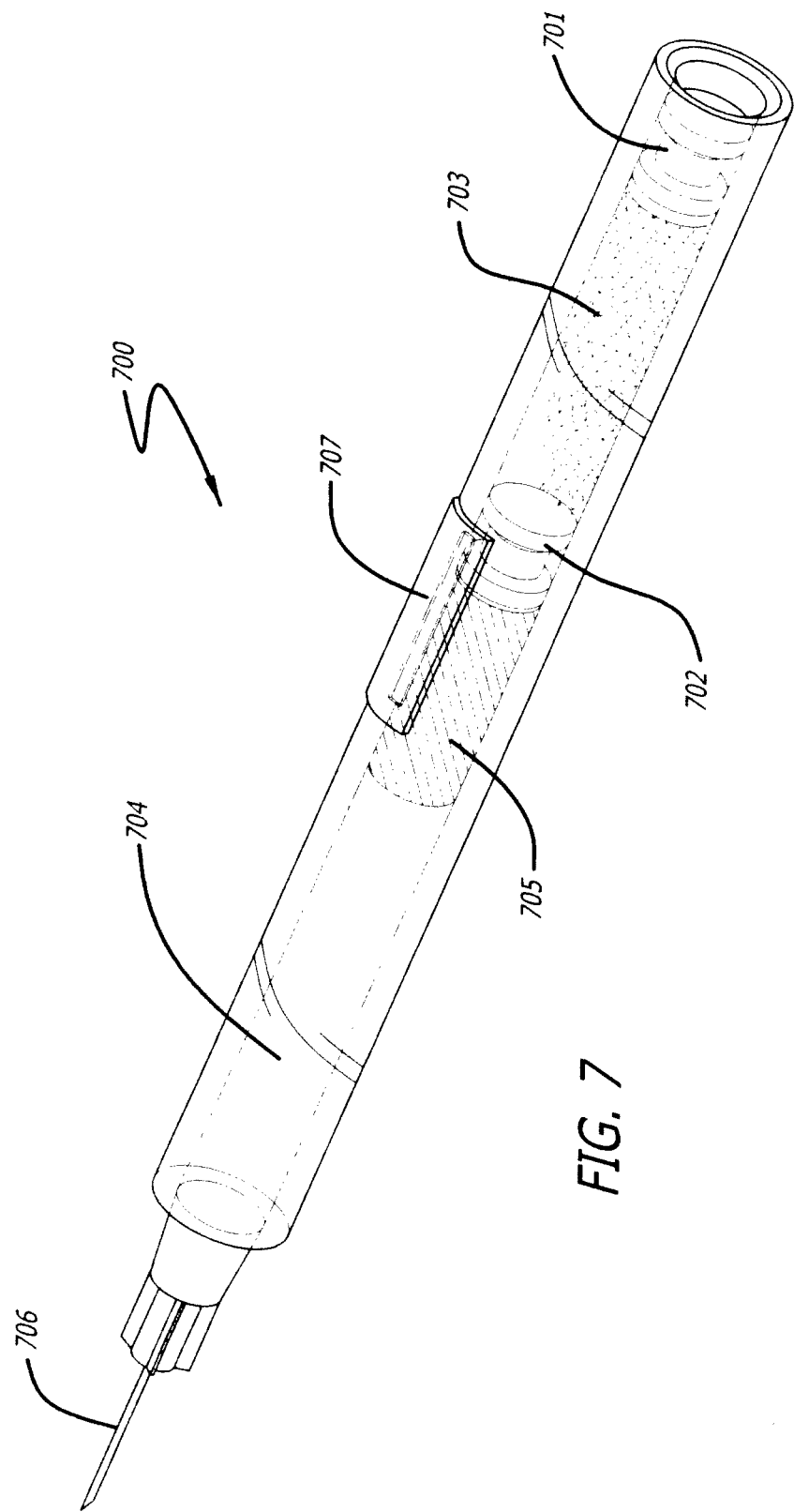
FIG. 7 is a simplified perspective view of some of the internal components of yet a still further embodiment of the invention.

A dual chamber cartridge is depicted in FIG. 7. One skilled in the art will understand that a multi-chamber cartridge is not limited to two chambers, but rather can have three or more. Multi-chamber cartridge 700 comprises at least two plungers. The first chamber 703 can be filled with a bioactive agent, a solvent, or any other appropriate fluid. Plunger 701 is advanced through chamber 703 thereby advancing the contents of chamber 703 into plunger 702 and thereby advancing plunger 702 to channel 707. Once plunger 702 reaches channel 707, the contents in chamber 703 are allowed to pass through channel 707 into chamber 704. The speed that the contents of chamber 703 are passed through channel 707 can be monitored and the force applied to plunger 701 can be adjusted to advance it at an appropriate rate. Chamber 704 can be filled with a bioactive agent, a solvent, or any other appropriate fluid. In one embodiment, chamber 704 can be at least partially filled with a solid form of a bioactive agent 705 which needs to be reconstituted. As plunger 701 advances toward plunger 702, the contents of chamber 703 are transferred to chamber 704 and mixed with, in one embodiment, a solid form of bioactive agent 705. Once plunger 701 reaches plunger 702, the contents can be allowed to mix (although there need not be a pause). Then, plungers 701 and 702 together are advanced towards the front of chamber 704 thereby extruding the mixture out of the needle 706.

In some embodiments, the contents of chamber 703 can be transferred to chamber 704 by other means than channel 707. In one embodiment, plunger 702 can be semi-permeable and then pressure is applied to plunger 701, the contents can be allowed to advance through the semi-permeable membrane. In another embodiment, a needle can be situated to puncture plunger 702 to allow the contents of chamber 703 to advance into chamber 704. Other possible plunger configurations are within the scope of the present description.

The Product

The injectable materials comprise one or more biocompatible materials. The materials include, but are not limited to, dermal fillers, hyaluronic acid-based dermal fillers (e.g. Juvèderm™ Ultra and Juvèderm™ Ultra Plus (Allergan, Irvine, Calif.)), hydrogels (i.e. superabsorbent natural or synthetic polymers), organogels, xerogels, encapsulated and/or cross-linked biomaterials, silicones, glycosaminoglycans (e.g. chondroitin sulfate, dermatin sulfate, dermatin, dermatin sulfate, heparin sulfate, hyaluronic acid, o-sulfated hyaluronic acid), polysaccharides (e.g. chitosan, starch, glycogen, cellulose), collagen, elastin, local anesthetics (e.g. Benzocaine, Chloroprocaine, Cyclomethycaine, Dimethocaine/Larocaine, Propoxycaine, Procaine/Novocaine, Proparacaine, Tetracaine/Amethocaine, Amino amides, Articaine, Bupivacaine, Carticaine, Cinchocaine/Dibucaine, Etidocaine, Levobupivacaine, Lidocaine/Lignocaine, Mepivacaine, Piperocaine, Prilocalne, Ropivacaine, Trimecaine), drugs, bioactive agents, antioxidants, enzyme inhibitors (e.g. anti-hyaluronidase), vitamins, minerals, water, saline, light curable or light activated materials, vaccines, and pH curable or pH activated materials. Other biocompatible materials not mentioned above are also considered within the scope of the present description.

The injectable materials may be made up of a first material and a second material that is mixed with the first material prior to injection, as described elsewhere herein. In some embodiments, the second material is a bioactive agent which facilities delivery of the first during injection (e.g. to reduce extrusion force). Additional bioactive agents may include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, anti-fungal agents, steroids, chemotherapeutic agents, analgesics, antibiotics, protease inhibitors, statins, nucleic acids, polypeptides, growth factors and delivery vectors including recombinant micro-organisms, liposomes, and the like. Combinations of additional bioactive agents are also within the scope of the present description.

Other injectable materials include toxins such as botulinum toxins. The botulinum toxin can be selected from the group consisting of botulinum toxin types A, B, $C_1$, D, E, F and G, a pure or purified (i.e. about 150 kD) botulinum toxin, as well as a native or recombinant botulinum toxin. The material can comprise between about 1 unit to about 20,000 units of the botulinum toxin or a therapeutically effective amount, and the composition can comprise an amount of botulinum toxin sufficient to achieve a therapeutic effect lasting between 1 month and 5 years. The botulinum toxin can be reconstituted within the device as described elsewhere herein or before the cartridge is placed in the device. The botulinum toxin can be reconstituted with sterile 0.9% sodium chloride (saline).

The dilution ratio can be 1 to 100 units of botulinum toxin per 0.1 mL of saline. More preferably, 1 to 50 units per 0.1 mL of saline, or 1 to 10 units per 0.1 mL of saline. In one embodiment, 4 units per 0.1 mL of saline can be used. The dilution ratio will be highly dependent on the type of botulinum toxin used or combination of botulinum toxins used.

Additional Features

Power to the device can be supplied by such means as a direct connection to an AC/DC power source, this can be accomplished using an electrical plug. Using a direct connection to a power source as described above requires that the devices be restrained by the power cord. In one embodiment, the devices are substantially entirely powered by one or more batteries located in the device shell. The batteries may be common non-rechargeable types such as, but not limited to, A, AA, AAA, C, D, and 9V. The one or more batteries used may be rechargeable batteries. The rechargeable battery(s) can be charged through induction or through direct-connect interface to an AC/DC power source. In one embodiment, the rechargeable battery(s) may be a permanent battery that charges within the devices and is not removed by the operator. The rechargeable battery(s) may be semi-permanent meaning they are charged inside the devices, but can be replaced if the battery(s) expire or malfunction over time. The rechargeable battery(s) may be operator replaceable of either standard or non-standard type batteries. The operator replaceable rechargeable batteries may be charged within the devices or outside the devices. The operator replaceable rechargeable batteries charged outside the devices can be specific for the devices and comprise a series of standby batteries ready for rapid swapping.

The devices can comprise one or more means of electronic storage. The storage can be built-in internal storage (e.g. random access memory, flash memory, read only memory, microdrive). The internal storage may be built directly into the PCB. The storage can be an external source. The device can comprise a slot to which an external storage device may be connected or inserted. Such external storage devices include, but are not limited to universal serial bus (USB) drives, firewire drives, flash and media cards, and microdrives.

The internal or external storage can contain information about the device and/or the cartridge or product associated with the device. The information can include, but is not limited to, operating software, firmware, device usage statistics, patient information, patient name, patient identification, Product name, Product part number, Product Rx number, Product lot number, Product expiration date, date of injection (s), time of injection(s), area(s) of injection(s), injection volume(s), injection volume(s) per area injected, total volume injected, and operator name.

The devices may further comprise a stand (not shown). The stand can function as a convenient place to store the device when it is not in use. The stand may further be used to charge the device. A single stand may comprise multiple devices. The stand can further comprise a port (e.g. USB, firewire)

from which data can be transferred to and from the device's internal or external storage or devices housed in the stand. The data can be synchronized with database software stored on a standalone or networked computer. The stand may further comprise the components to wirelessly network the injection device and its data contents for retrieval wirelessly throughout a network.

The devices can be fitted with a power speaker driven by the power source and controlled by the PCB. The speaker can produce audible tones when the device needs attention. Such instances that may require attention include, but are not limited to, low battery power, empty cartridge, confirmation of a setting, power on and power off.

The devices may have an outer tip that can come into contact with the patient's skin at the future site of injection. The tip may be cooled, thereby reducing the pain associated with needle punctures through the skin. The tip can be made of a metal or metal alloy. The cool touch of metal alone may be all that is required to reduce the pain associated with a needle puncture, but more extreme cooling may be required. Methods of cooling are known in the art and may include liquid nitrogen and/or a Peltier device.

The devices described herein can further comprise at least one light source. The light source may be fixed or adjustable. In one embodiment, the light source can be a source of visible light such as an LED, to assist the operator in viewing the site of injection. In one embodiment, the light source is ultraviolet (UV). UV light can be used to cure or activate the Product that has been injected into the skin. The wavelength of UV light used can be determined by the operator depending on the absorption spectrum of the Product being injected. In one embodiment, the light may be produced by a laser, such as a laser pointer. The laser pointer light can assist an operator in precisely controlling the location of the injection.

The injection devices described herein can inject materials that are difficult or even impossible to inject manually using a conventional syringe and plunger due to the high extrusion forces necessary to inject them. The present devices are capable of injecting such materials in a highly controlled, precise manner through a various range of needle gauges. The needle gauge can be at least 10 G to as high as 50 G. For example, the needle gauge may be a gauge in a range of between about 23 G to about 34 G, for example, between about 27 G to about 32 G. The devices can deliver Product at a rate of about 0.001 to about 1 mL/sec. More preferable injection speeds can be between 0.004 to 0.05 mL/sec. The rate of delivery is highly dependent of the viscosity of the Product being delivered and the density of the tissue being injected. Generally, a highly viscous Product will require a higher extrusion force relative to a required extrusion force for a relatively lower viscosity Product. The devices described herein can inject the material, for example, at the desired rate, with extrusion forces of at least about 50 Newtons (N) and up to about 200 N.

Figure 9:
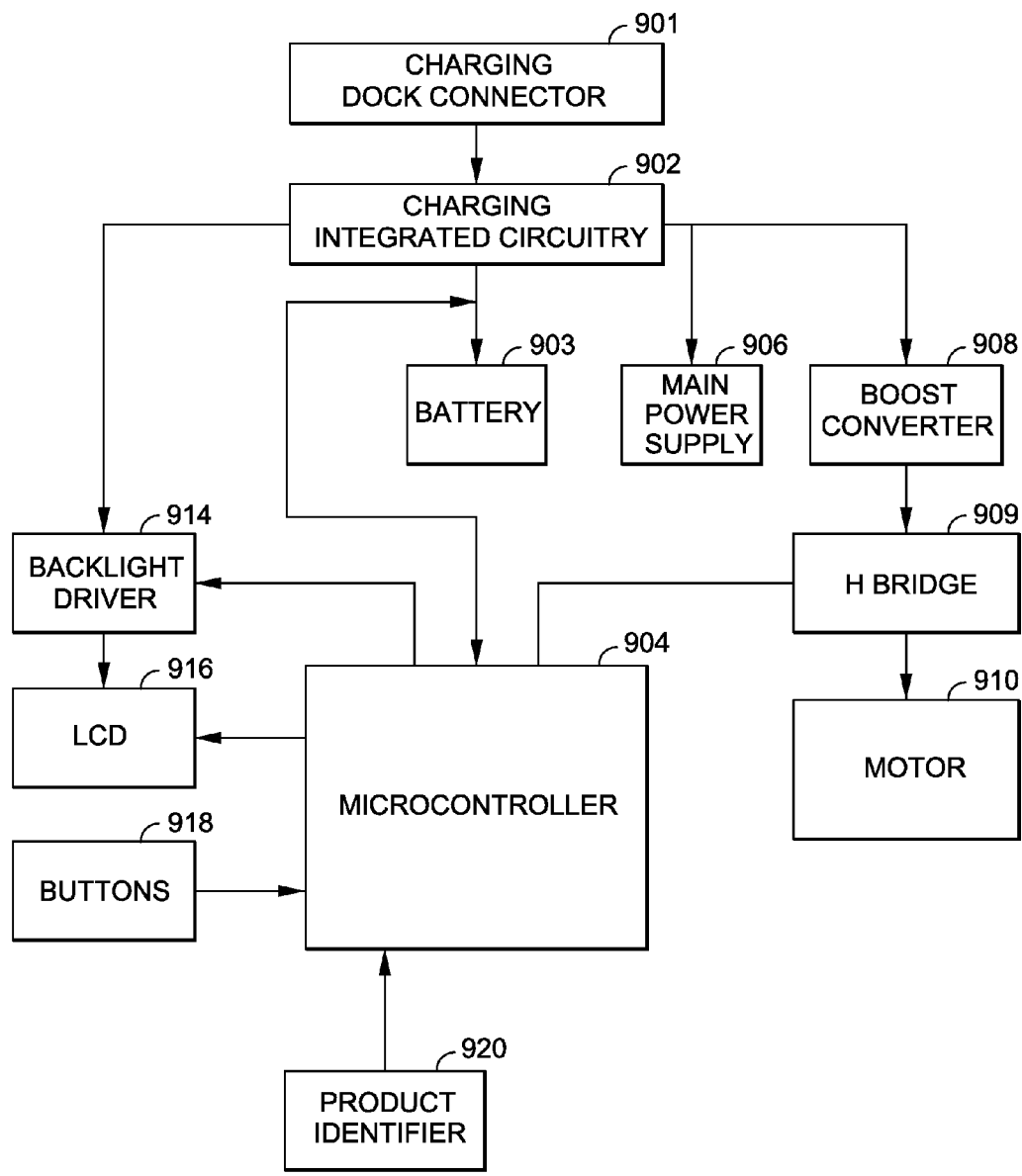
FIG. 9 depicts a logic/block diagram of some of the internal components of any of the embodiments shown elsewhere herein.

FIG. 9 depicts a logic diagram of the internal components in an exemplary embodiment of the invention.

The device components may include a charging dock connector 901, charging integrated circuitry 902 which manages the charging and discharging of the battery 903, for example a rechargeable lithium-ion cell battery, which is the main power source for the device, and reports status changes to the programmable microcontroller 904. A 3.0V power supply 906, provides power for the circuitry. A boost converter 908 creates 5V that is used to drive the motor 910. H Bridge 909 controls the speed and direction of the motor 910, for example a DC motor, which is used to drive the piston in the cartridge (piston and cartridge not shown in FIG. 9). A backlight driver 914 activates a backlight on the liquid crystal display screen 916. Buttons 918 allow for user input, for example, of a desired injection rate. A product identifier 920 reads the cartridge (not shown) as described elsewhere herein, and through microcontroller 904, notifies the user of the product in the cartridge. In an exemplary embodiment, buttons 918 include a pressure sensitive switch, for example, a commercially available, a thin, flexible piezoresistive force sensor called FlexiForce model no. A201 in the 0-251b (110 N) force range, manufactured by Tekscan.

The components can work together to sense cartridges that are inserted into the device. The device can include sensors (as described infra) capable of detecting correct insertion of different types of injection cartridges. The cartridges can be marked by features such as bumps, flags, light and dark lines, or other means known in the art.

The device may have the ability to drive a motor at variable speeds to facilitate different rates of delivery of the Product. The microcontroller can have the ability to run the motor in both rotational directions. Additionally, the device may have sensors to quantify the velocity of the drive train and verify the desired delivery rate. The sensors may provide feedback to the microcontroller allowing it to drive the motor faster or slower if the desired delivery rate is not being met.

In one embodiment, upon actuation of the inject button, a signal can be sent to the microcontroller and therein the software may drive the motor forward at the proper velocity for the desired injection rate. The software can implement one or more algorithms to maintain the injection rate during variations in resistance from the cartridge and/or the drive train.

In one embodiment, upon release of the inject button, the software and microcontroller shall drive the motor in reverse to full speed for a predetermined distance in order to release the pressure on the cartridge. This can allow for more precise delivery of Product and can prevent leaking.

In one embodiment, in the event that the microprocessor detects the entire contents of the cartridge have been expelled, the microprocessor can reverse the motor as described above and present an "empty cartridge" warning on the display.

In one embodiment, upon detection by the microprocessor, based on feedback from sensors, that the desired injection rate cannot be attained, the motor may reverse as though the inject button was released, and a warning message may be displayed. This situation could result from situations such as, but not limited to, an improperly inserted cartridge, a blockage preventing delivery of the Product, a mechanical failure or combinations thereof.

In some embodiments, the devices described herein can deliver Products or inject into areas of tissue that require high precision. As such, the devices can have one or more, in some cases two or more, sensors which monitor the device's precision. In some embodiments, the sensors or systems can be redundant.

In some embodiments, the Products to be delivered may be non-Newtonian or mixtures of Newtonian and non-Newtonian fluids. Such fluids can have inconsistent and/or unpredictable force-to move requirements which may utilize the redundant features described above. Such products can have high yield points requiring high stall torque requirements. Non-Newtonian fluids may have high yield points but have rapid drops in force-to-move requirements after the yield point is overcome. As such, the devices described herein can accommodate for rapid changes in extrusion force requirements.

In one embodiment, the devices can achieve a steady state of material delivery despite the changes in fluid consistency and/or viscosity, including differing yield points. Additionally, in some embodiments, two or more different materials can be utilized requiring enough force to overcome two or more different yield points at two or more different times during injection. As such, the devices can be equipped with electronics that can constantly monitor the delivery force, speed, and cartridge pressure to name a few. In addition, those devices may be designed such that the plunger may be backed up at the termination of product dispensation in order to avoid over-dispensing Product due to, for example, pressure build up in the Product cartridge during administration.

Figure 10:
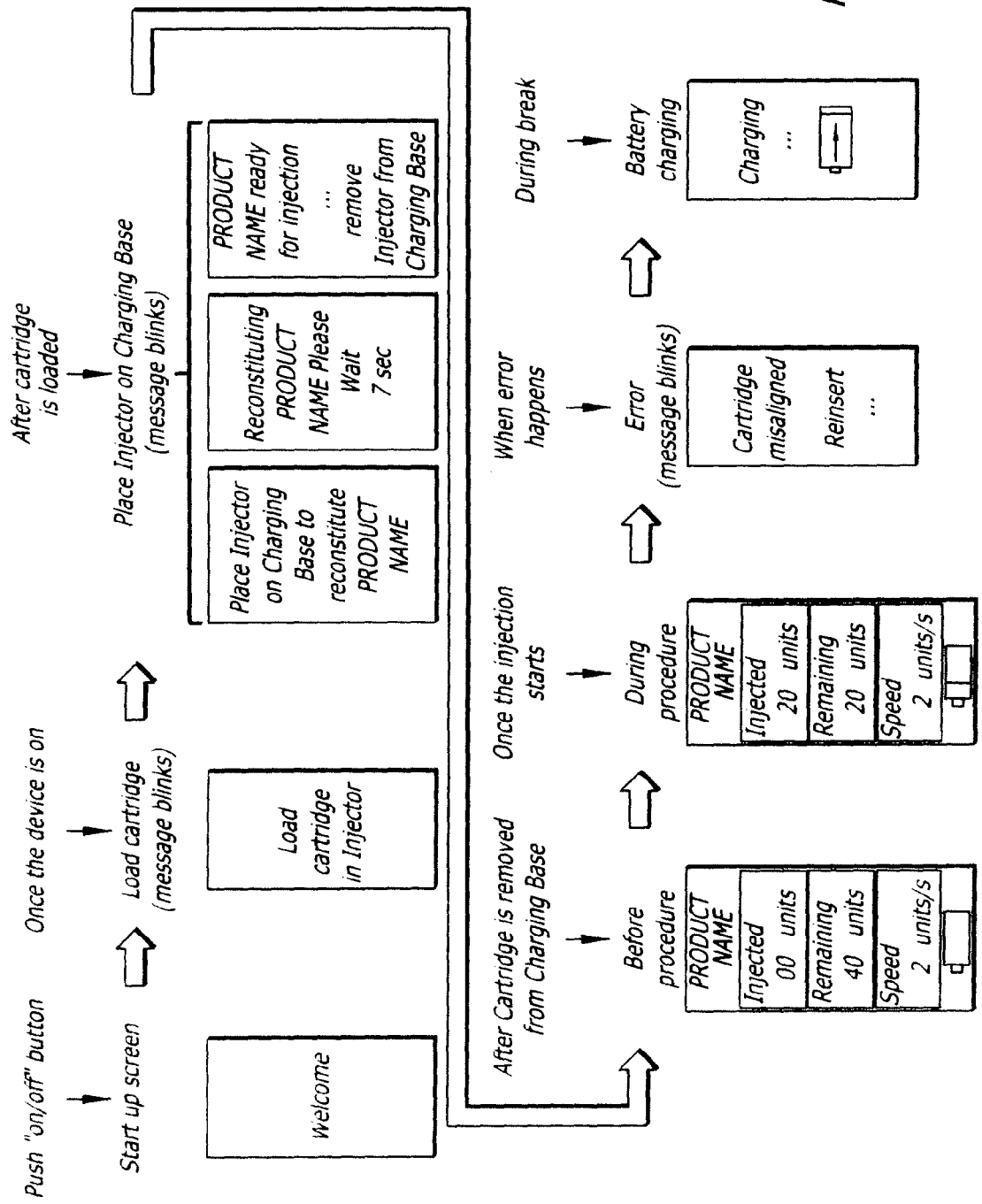
FIG. 10 depicts various examples of possible display screens of any of the injection devices shown elsewhere herein.

FIG. 10 depicts non-limiting display screen variations that may be used with the devise described herein. In one embodiment, a welcome screen is displayed. In another embodiment, the display screen can instruct the operator to insert a cartridge or even to reinsert a cartridge if it is not inserted correctly. In one embodiment, if the device is using a cartridge that requires reconstitution, the display screen may instruct the operator to reconstitute the Product or to insert the device in its base for reconstitution of the Product. In one embodiment, the display screen can display information prior to, during and after injection showing such information as, but not limited to, product name, number of units injected, current, past and present injection speeds, and battery life. In one embodiment, when the device is placed in its base, it can be charged and the display can indicate the device is being charged.

Figure 11:
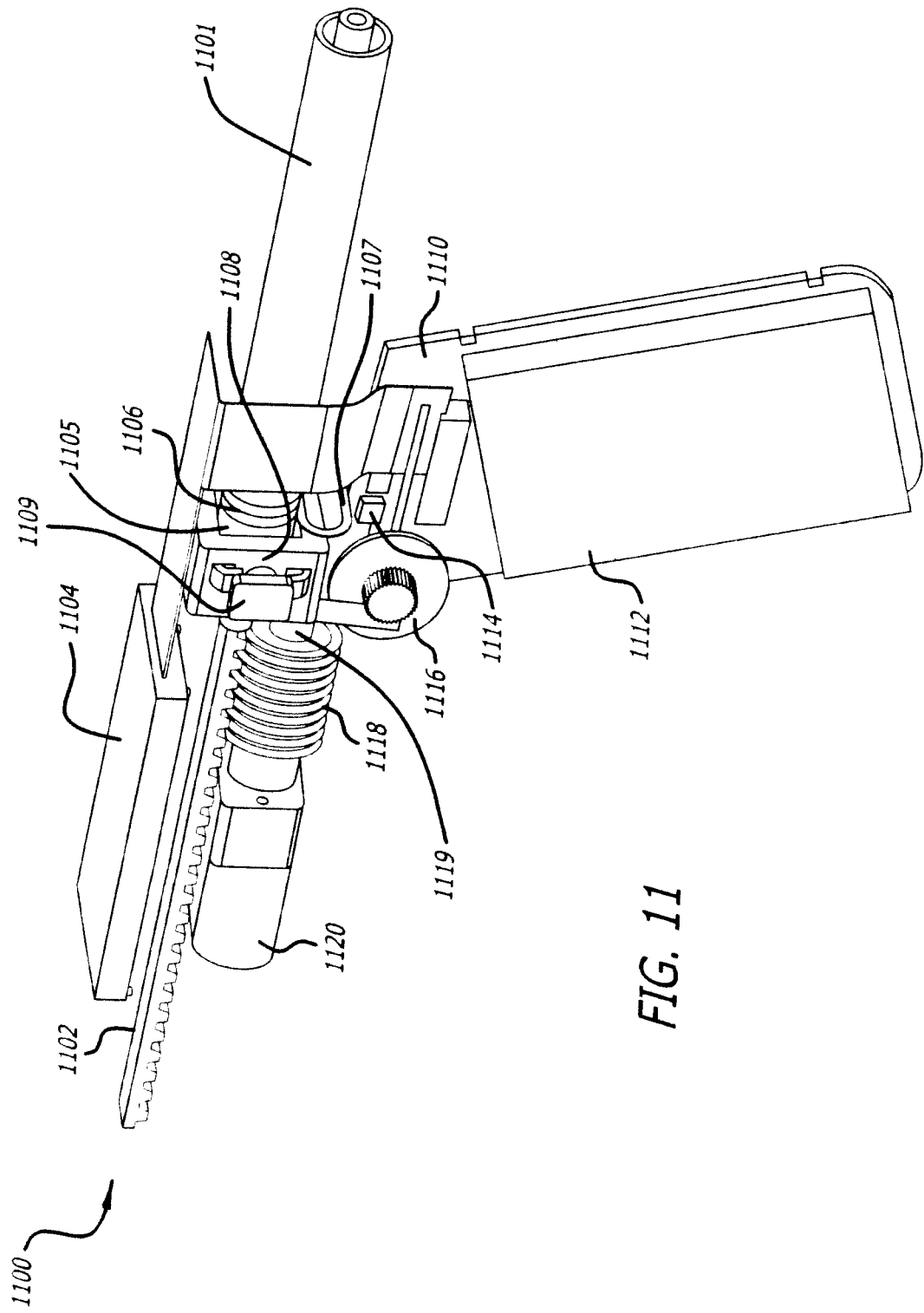
FIG. 11 depicts a non-limiting combination of components housed in an inner body of a device of the invention, for example, the device shown in FIGS. 8A and 8B.

FIG. 11 depicts a non-limiting combination of internal components 1100 housed in the inner body of a device as described herein. One skilled in the art will appreciate that the components may be situated differently depending on the configuration of the inner body and/or the shape of the outer body of the device. In one embodiment, the internal components of FIG. 11 may be used in conjunction with the device in FIG. 8. Combination of internal components 1100 comprises a motor 1120 which turns worm gear 1118, thereby driving rack 1102. Rack 1102 engages the plunger (not shown) in posterior end 1105 of cartridge 1101. PCB 1110 can gather and send information to optical encoder 1116, microswitch 1114, cartridge locking/ejection mechanism 1108, and screen 1104. The PCB 1110 and screen 1104 are powered by battery 1112. In one embodiment, optical encoder 1116 can accurately determine the position, speed and direction of the rack 1102 by counting the number of turns and turn direction of motor shaft 1119. In one embodiment, microswitch 1114 is activated when lever arm 1107 is flexed downward and makes contact with microswitch 1114. Lever arm 1107 is flexed downward every time it passes over cartridge detent 1106 until cartridge 1101 is fully inserted and engaged into locking/ejection mechanism 1108. The number of cartridge detents can vary, depending on the type of product and/or product volume in cartridge 1101. The number of microswitch activations is relayed to PCB 1110 and PCB 1110 identifies the cartridge inserted. When cartridge 1101 is identified, PCB 1110 communicates this information to motor 1120 to drive rack 1102 to the appropriate starting location and also to the display on screen 1104 to inform the operator of the product type (name) and initial (or remaining) product volume. In one embodiment, cartridge 1101 is unlocked and is partially ejected from the device when the user simultaneously presses both eject buttons 1109 (only one shown) of cartridge locking/ejection mechanism 1108. This generally occurs after the user has injected the full contents of the cartridge.

EXAMPLE 1

Extrusion experiments were performed on 0.8 mL Schott TopPac® (SCHOTT North America, Inc., Lebanon, Pa.) syringe fitted with a Tyco 30 G×½" needle. Juvèderm™ Ultra (Allergan Inc., Irvine, Calif.) was extruded from the needle to assess the force needed to extrude the highly viscous hyaluronic acid-based dermal filler through a 30 G needle. The results in Table 1 show the results of the experiments.

TABLE 1

| Plunger Rate (mm/min) | Plunger Rate (mm/sec) | Approximate Injection Rate* (mL/sec) | Approximate Force Required (N) |
|---|---|---|---|
| 20 | 0.333 | 0.006 | 23 |
| 50 | 0.833 | 0.015 | 35 |
| 100 | 1.667 | 0.029 | 47 |
| 150 | 2.500 | 0.044 | 60 |

*Schott 0.8 mL syringe, the gradient is: 5.7 mm is approximately 0.1 mL

For example, to inject the total contents of the syringe at a rate of 0.006 mL/sec, the plunger must travel approximately 46 mm in a time of approximately 2.3 min (approximate plunger rate of 20 mm/min).

Results showed that depending on the desired injection rate, large forces are required to advance the plunger and inject the viscous dermal filler. It is quite easy to see why manual injection with a traditional plunger style syringe would be quite difficult to control and inject at the same time. The device described herein can provide the appropriate force for a given injection speed while eliminating operator error in injection and patient pain associated with it.

EXAMPLE 2

This example refers to the device 100 depicted in FIG. 1A-1C, the electronic display screen 400 in FIG. 4, and the injection components of the inner body depicted in FIG. 5.

The operator turns on the device 100 by depressing power button 105. The electronic display 106 (which may comprise screen 400 in FIG. 4) will power on and indicate the device status as 'cartridge not loaded.' The device is then set-up to provide an audible beep to alert the operator as to the status 'cartridge not loaded.' The operator proceeds to slide the cartridge into the hole at the front of the device in cap 107. The hole in cap 107 reveals the cartridge chamber in the inner body of the device. The cartridge is slid into the device until it clicks in place. The device then reads the RFID off the cartridge and presents the appropriate data on display 106. Once the data is uploaded from the RFID and processed by the device, 'Ready' will be presented on display 106. The operator can then adjust the injection speed by using a combination of + and − buttons 103 and 104, or through the menu driven multi-button 108. If using buttons 103 and 104, the injection speed can be changed even during the injection. If the menu driven multi-button 108 is used, the speed of injection must be selected in the menu and must be set using multi-button 108 and confirmed using button 109. Thereafter, the speed of the injection cannot be changed during the injection.

The operator then installs an appropriate needle 112 onto the luer-tip 113 at the exposed end of the cartridge. The sheath around the needle is then removed. The area for injection is cleaned appropriately. The needle is punctured through the skin at the appropriate location of a patient and inject button 102A or 102B is pressed. The Product is dispensed from the device and an audible beep signals the operator that the injection is complete. The needle is removed from the patent and discarded appropriately. The needle and cartridge can be ejected from the device safely by pressing eject button 110, thereafter, the cartridge and needle will fall from the device as a single unit (preferably into an appropriate biohazard container) when the device is angled downward. The operator can then power the device off by pressing and holding power button 105.

EXAMPLE 3

This example refers to the device 100 depicted in FIG. 1A-1C, the electronic display screen 400 in FIG. 4, and the components of the inner body depicted in FIG. 6.

The operator turns on the device 100 by depressing power button 105. A red LED illuminates indicating the device is not ready for injection. The electronic display 106 will power on and indicate the device status as 'cartridge not loaded.' The device can be set-up to provide an audible beep to alert the operator as to the status 'cartridge not loaded.' The operator proceeds to slide a cartridge of dried botulinum toxin Type A into the hole at the front of the device in cap 107. The hole in cap 107 reveals the cartridge chamber in the inner body of the device. The cartridge is slid into the device until it clicks in place. The device then reads the RFID off the cartridge and presents the appropriate data on display 106. Once the data is uploaded from the RFID and processed by the device, the device indicates to the operator that saline needs to be loaded, by displaying 'load saline vial' on display 106. The operator loads a saline vial into the device through a separate opening in the device until it snaps into place.

Then, display 106 indicates 'adjust dose setting.' The operator inputs the appropriate dose using multi-button 108 and locks in the dose using set button 109. Then, display 106 will indicate 'reconstitute product'. The operator depresses set button 109 on the device. The device reconstitutes the botulinum toxin and gently mixes it for a predetermined amount of time. Thereafter, the red LED with turn green indicating the Product is ready for injection and 'ready' will be presented on display 106. The operator can then adjust the injection speed by using a combination of buttons 103 and 104, or through the menu driven multi-button 108. If using buttons 103 and 104, the injection speed can be changed even during the injection. If the menu driven multi-button 108 is used, the speed of injection must be selected in the menu and must be set using set button 109. Thereafter, the speed of the injection cannot be changed during the injection.

The operator then installs an appropriate needle 112 onto the luer-tip 113 at the exposed end of the cartridge. The sheath around the needle is then removed. The area for injection is cleaned appropriately. The needle is punctured through the skin at the appropriate location of a patient and inject button 102A or 102B is pressed. The Product is dispensed from the device and an audible beep signals the operator that the injection is complete. The needle is removed from the patent and discarded appropriately. The needle and cartridge can be ejected from the device safely by pressing eject button 110, thereafter, the cartridge and needle will fall from the device as a single unit (preferably into an appropriate biohazard container) when the device is angled downward. The operator can then power the device off by pressing and holding power button 105.

EXAMPLE 4

Figure 8:
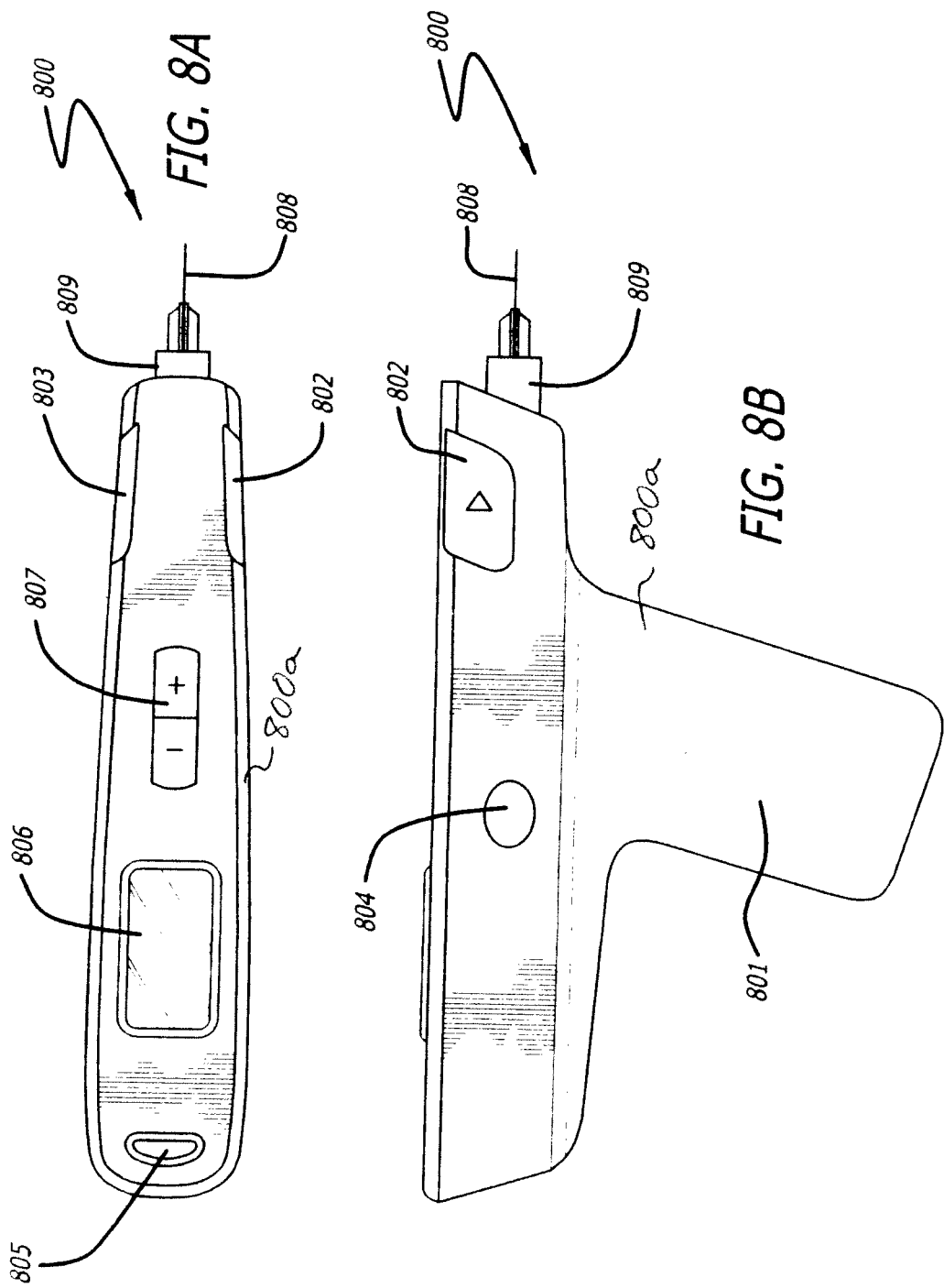
FIGS. 8A and 8B show top and side views of another embodiment of the invention.

This example refers to the device 800 depicted in FIG. 8, the electronic display screen in FIG. 4, the cartridge in FIG. 7 and the injection components of the inner body depicted in FIG. 5.

The operator turns on the device by holding down power/select button 805. A red LED illuminates indicating the device is not ready for injection. The electronic display 806 will power on and indicate the device status as 'cartridge not loaded.' The device can be set-up to provide an audible beep to alert the operator as to the status 'cartridge not loaded.' The operator proceeds to slide a multi-chamber cartridge as seen in FIG. 7 into the hole at the front of the device. The hole at the front of the device reveals the cartridge chamber in the inner body of the device. The cartridge is slid into the device until it clicks in place. The device then reads the RFID off the cartridge and presents the appropriate data on display 806. Once the data is uploaded from the RFID and processed by the device, the device indicates to the operator that the saline needs to be gently mixed into the lyophilized botulinum toxin Type A by showing 'ready to reconstitute' on display 806. The operator pushes power/select button 805 to accept the request and the saline is gently mixed into the lyophilized botulinum toxin. After mixing is completed and the appropriate time has elapsed, the display 806 reads 'adjust dose setting.

The operator inputs the appropriate dose using multi-button 807 and locks in the dose using power/select button 805. Thereafter, the red LED with turn green indicating the Product is ready for injection and 'ready' will be presented on display 806. The operator can then adjust the injection speed by using a combination of multi-button 807 and power/select button 805.

The operator then installs an appropriate needle 808 onto the luer-tip at the exposed end of the cartridge 809. The sheath around the needle is then removed. The area for injection is cleaned appropriately. The needle is punctured through the skin at the appropriate location of a patient and inject button 802 or 803 is pressed. The Product is dispensed from the device and an audible beep signals the operator that the injection is complete. The needle is removed from the patent and discarded appropriately. The needle and cartridge can be ejected from the device safely by pressing eject button 804, thereafter, the cartridge and needle will fall from the device as a single unit (preferably into an appropriate biohazard container) when the device is angled downward. The operator can then power the device off by holding down power/select button 805.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A hand-held injection device for soft tissue comprising:
   a cartridge suitable for containing a dermal filler material and couplable to a needle;
   a shell structured to contain the cartridge;
   a motorized drive mechanism;
   a power source for activating the drive mechanism;
   a user-programmable controller coupled to the drive mechanism, where a user-defined injection rate can be set;
   a vial, suitable for containing a dilutant for the dermal filler material, fluidly coupled to the cartridge;
   a pump and a one-way valve for directing the dilutant into the cartridge to be mixed with the dermal filler material; and
   a plunger actuated by the drive mechanism for forcing the dermal filler material mixed with the dilutant from the cartridge and out of the needle at the user defined injection rate.

2. The device of claim 1 wherein said user-defined injection rate can be set at a rate between about 0.001 mL/sec and about 1 mL/sec.

3. The device of claim 1 which is capable of injecting the dermal filler material mixed with the dilutant from the cartridge through a needle having a gauge of between about 23 G to about 34 G.

4. The device of claim 1 which is capable of injecting the dermal filler material mixed with the dilutant through a needle having a gauge of between about 27 G to about 32 G.

5. The device of claim 1 capable of injecting the dermal filler material mixed with the dilutant through a needle having a length of between about ¼ inch (6 mm) to about 2 inches (50 mm).

6. The device of claim 1 capable of injecting the dermal filler material mixed with the dilutant through a needle having a length of between about ½ inch (10 mm) to about 1 ½ inches (40 mm).

7. The device of claim 1 wherein the cartridge is substantially cylindrical and has an inner diameter of between about 0.25 inch (6.3 mm) to about 1 inch (25 mm).

8. The device of claim 1 wherein the cartridge is substantially cylindrical and has an inner diameter of between about 0.18 inch (4.6 mm) to about 0.35 inch (8.9 mm).

9. The device of claim 1 wherein the power source is a battery contained in the shell.

10. The device of claim 1 requiring no external power source to operate.

11. The device of claim 1 which is self-contained.

12. The device of claim 1 wherein the dermal filler material is a hyaluronic acid-based dermal filler that is at least partially crosslinked.

13. The device according to claim 1 further comprising a second motor for agitating the dermal filler material and dilutant mixture in the cartridge.

14. The device according to claim 13 further comprising a weight fitted with the motor.

15. The device of claim 14 wherein the motor causes the weight to spin out of balance which agitates the cartridge to effect the mixing.

* * * * *

UNITED STATES PATENT AND TRADEMARK OFFICE
CERTIFICATE OF CORRECTION

PATENT NO. : 8,801,659 B2
APPLICATION NO. : 12/994568
DATED : August 12, 2014
INVENTOR(S) : Christopher S. Mudd et al.

Page 1 of 1

It is certified that error appears in the above-identified patent and that said Letters Patent is hereby corrected as shown below:

On Title Page 2, in column 2, References Cited under "Other Publications", line 3, delete "Publishiers" and insert -- Publishers --, therefor.

In the Specification

In column 11, line 35, delete "Prilocalne," and insert -- Prilocaine, --, therefor.

In column 14, line 9, delete "0-251b" and insert -- 0-25 lb --, therefor.

Signed and Sealed this
Tenth Day of March, 2015

Michelle K. Lee
*Deputy Director of the United States Patent and Trademark Office*